United States Patent
Blake et al.

(10) Patent No.: US 11,609,917 B1
(45) Date of Patent: *Mar. 21, 2023

(54) CHEMICAL FORMULA EXTRAPOLATION AND QUERY BUILDING TO IDENTIFY SOURCE DOCUMENTS REFERENCING RELEVANT CHEMICAL FORMULA MOIETIES

(71) Applicant: Purdue Pharma L.P., Stamford, CT (US)

(72) Inventors: Paul Blake, Newtown, PA (US); Kevin Brogle, Cream Ridge, NJ (US); Kevin Brown, Philadelphia, PA (US); Don Kyle, Yardley, PA (US)

(73) Assignee: ACCENCIO LLC, Philadelphia, PA (US)

( * ) Notice: Subject to any disclaimer, the term of this patent is extended or adjusted under 35 U.S.C. 154(b) by 1216 days.

This patent is subject to a terminal disclaimer.

(21) Appl. No.: 16/111,081

(22) Filed: Aug. 23, 2018

Related U.S. Application Data

(63) Continuation of application No. 14/795,375, filed on Jul. 9, 2015, now Pat. No. 10,372,713.

(60) Provisional application No. 62/023,006, filed on Jul. 10, 2014.

(51) Int. Cl.
*G01N 33/48* (2006.01)
*G06F 16/2457* (2019.01)
*G06Q 50/18* (2012.01)
*G06F 16/93* (2019.01)
*G06F 16/248* (2019.01)

(52) U.S. Cl.
CPC ...... *G06F 16/24575* (2019.01); *G06F 16/248* (2019.01); *G06F 16/93* (2019.01); *G06Q 50/184* (2013.01)

(58) Field of Classification Search
None
See application file for complete search history.

(56) References Cited

U.S. PATENT DOCUMENTS

| | | |
|---|---|---|
| 5,345,516 A | 9/1994 | Boyer |
| 5,715,450 A | 2/1998 | Ambrose |
| 8,433,723 B2 | 4/2013 | Smith |
| 9,031,977 B2 | 5/2015 | Smith |
| 2002/0063739 A1 | 5/2002 | Gosden |
| 2002/0143725 A1 | 10/2002 | Smith |
| 2005/0060102 A1 | 3/2005 | O'Reilly |
| 2006/0116825 A1 | 6/2006 | Webb |
| 2007/0043511 A1 | 2/2007 | Jensen |
| 2015/0142730 A1* | 5/2015 | Dakshanamurthy .... H04L 67/10 707/609 |

OTHER PUBLICATIONS

Hagenbuchner, Markus, Alessandro Sperduti, and Ah Chung Tsoi. "A self-organizing map for adaptive processing of structured data." IEEE transactions on Neural Networks 14.3 (2003): 491-505.*
Durant, Joseph L., et al. "Reoptimization of MDL keys for use in drug discovery." Journal of chemical information and computer sciences 42.6 (2002): 1273-1280.*
Kohonen, Teuvo. "Essentials of the self-organizing map." Neural networks 37 (2013): 52-65.*
Tsuda, Nobuo, and Talsuyuki Shimizu. "Reconfigurable mesh-conneclcd processor arrays using row-column bypassing and direcl replacement." Parallel Archileclures, Algorilhms and Nelworks, 2000, I-SPAN2000. Proceedings. International Symposium on IEEE, 2000.
Foundations of Computer Science at Cenage Learning by Behrouz Forouzan and Firouz Mosharraf (2008) presenation [online] [retrieved on May 16, 2018] <URL:https://kiambi.kau.edu.sa/GetFile.aspx?id=64681 &Lng=AR&fn=ch-11.pt>.
Kim et al.. "Optimizing multidimensional index trees for main memory access." ACM SIGMOD Record. vol. 30. No. 2. ACM (2001) pp. 139-150).
Kikuchi, A. et. al., "Development of Self-Compressing BLSOM for Comprehensive Analysis of Big Sequence Data," BioMed Research International, vol. 2015, 8 pages. 2015.
Waddell, J., "Bioactivity landscape modeling: Chemoinformatic characterization of structure—activity relationships..," Bioorg. Med. Chem. 20 (2012) pp. 5443-5452.
Borkowska, E. et al., "Molecular subtyping of bladder cancer using Kohonen selforganizing maps," Cancer Medicine 2014; 3(5): 1225-1234.
Noeske, T, et. al., "Predicting Compound Selectivity by Self-Organizing Maps: Cross-Activities of Metabotropic Glutamate Receptor Antagonists," ChemMedChem 2006, 1, 1066-1068.
Medina-Franco, J. et. al., "Visualization of the Chemical Space in Drug Discovery," Current Computer-Aided Drug Design, 2008, vol. 4, No. 4, pp. 322-333.
Osolodkin, D. et al., "Progress in visual representations of chemical space," Expert Opin. Drug Discov. vol. 10, No. 9 pp. 1-15 (2015).
Bote, V. et a., "Document organization using Kohonen's algorithm," Information Processing and Management, vol. 38, pp. 79-89. 2002.

(Continued)

*Primary Examiner* — Anna Skibinsky
(74) *Attorney, Agent, or Firm* — Leason Ellis LLP

(57) ABSTRACT

A system and method for extrapolating a set of specific representational identifiers that are represented or covered by a generic representational identifier found in a target document. Queries are constructed and performed on a corpus of source documents in which members of the extrapolated set of specific representational identifiers are compared to a database of representational data. By matching representational data in this way, any overlap between the generic representational data and specific instances of the generic representational identifier within the source documents is determined. In a more specific implementation, the system and method reduces the scope of the generic representational identifier such that the reduced scope generic representational identifier encompasses only novel specific representational identifiers.

10 Claims, 15 Drawing Sheets

(56) References Cited

OTHER PUBLICATIONS

Virshup, A. et al., "Stochastic Voyages into Uncharted Chemical Space Produce a Representative Library of All Possible Drug-Like . . . ," J. Am. Chem. Soc. 2013, 135, 7296-7303.
Owen, J. et. al., "Visualization of Molecular Fingerprints," American Chemical Society, J. Chem. Inf. Model. 2011, 51, 1552-1563.
Merlo, P. et. al., "Learning Document Similarity Using Natural Language Processing," Linguistik online 17, pp. 99-115. May 2003.
Digles, D. et al., "Self-Organizing Maps for In Silico Screening and Data Visualization," Molecular Informatics, vol. 30, pp. 838-846. 2011.
Kireeva, N. et. al., "Generative Topographic Mapping (GTM): Universal Tool for Data Visualization, Structure-Activity Modeling and . . . ," Mol. Inf. vol. 31, pp. 301-312. 2012.
Pascolutti, M. et. al., "Capturing Nature's Diversity," PLOS one, vol. 10, No. 4., pp. 1-12, Apr. 22, 2015.
Farkas, J., "Using Kohonen Maps to Determine Document Similarity," Centre for Information Technology Innovation (CITI), pp. 1-6.

* cited by examiner

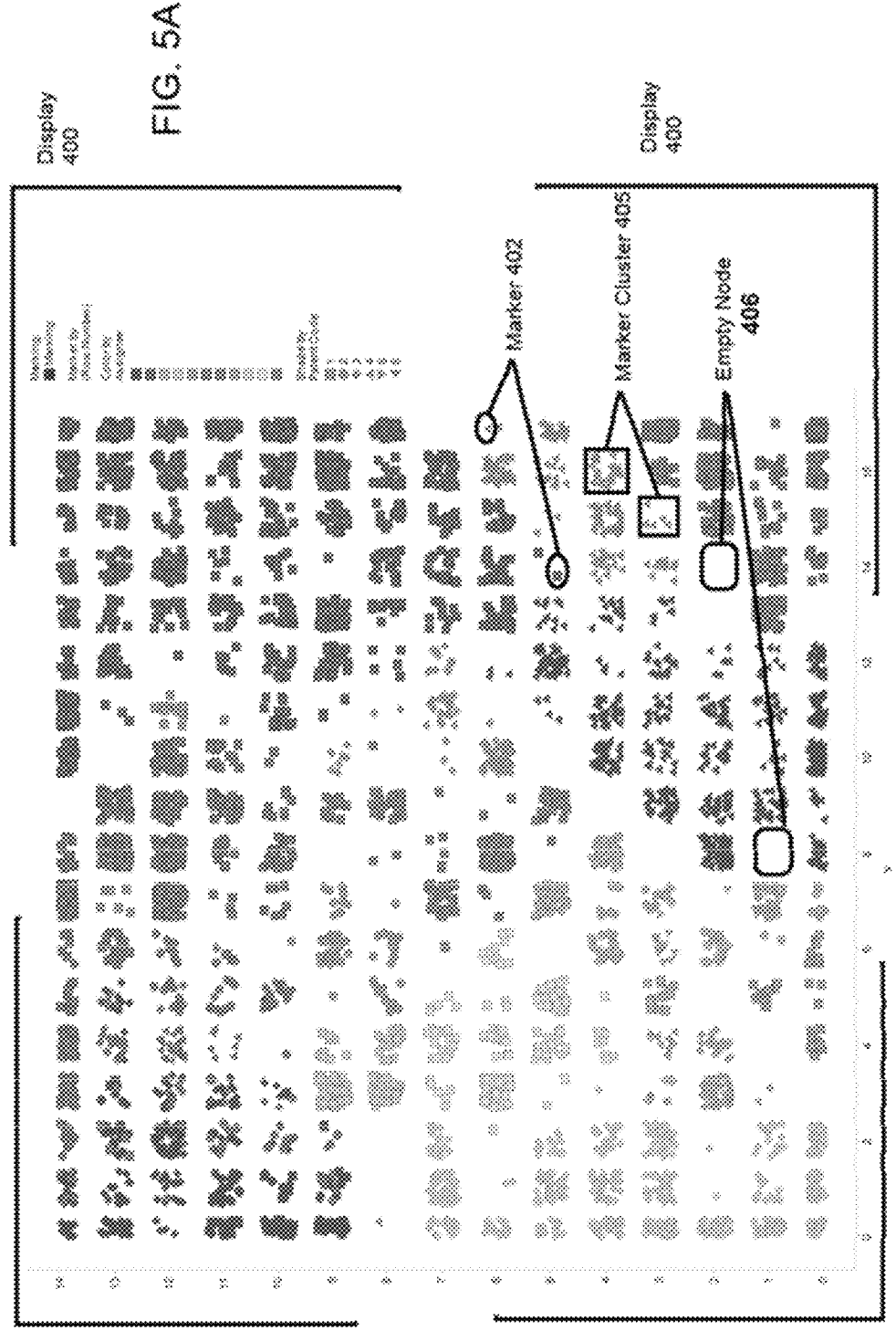

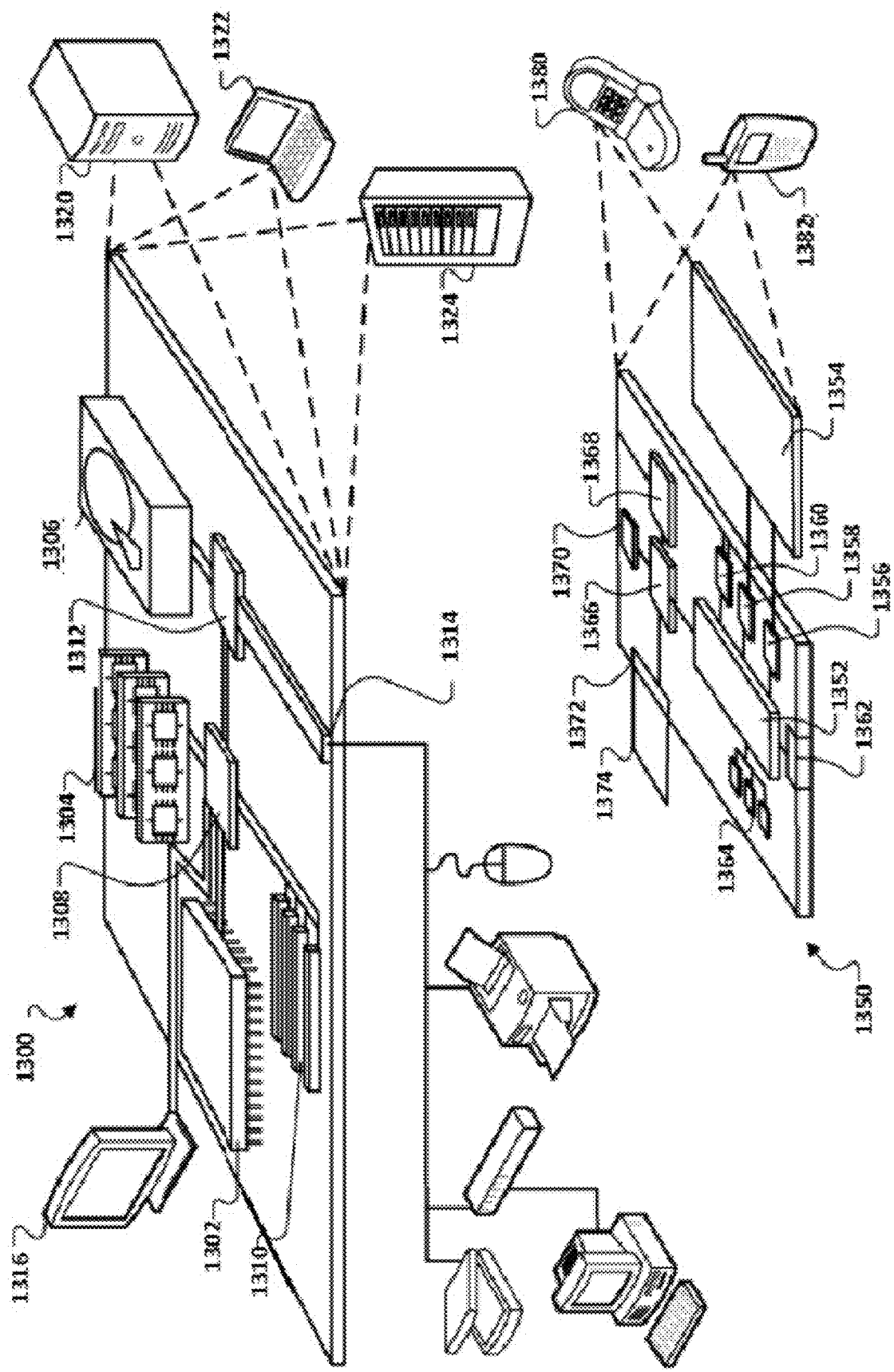

CHEMICAL FORMULA EXTRAPOLATION AND QUERY BUILDING TO IDENTIFY SOURCE DOCUMENTS REFERENCING RELEVANT CHEMICAL FORMULA MOIETIES

CROSS-REFERENCE TO RELATED APPLICATION

This application is a Continuation Application of U.S. application Ser. No. 14/795,375, filed on Jul. 9, 2015, which claims the benefit of priority under 35 U.S.C. Section 119 of U.S. Provisional Application Ser. No. 62/023,006, filed on Jul. 10, 2014, entitled "System and Method for Predicting New Chemical Entities," which are hereby incorporated by reference as if set forth in their entireties herein.

FIELD OF THE INVENTION

The present invention relates to extracting generic chemical formula data from a document and, more particularly to visual indications of overlapping and non-overlapping data within a body of source documents, and also to an analysis of a landscape comprising chemical moieties and possibly other subject matter within the landscape.

The present invention concerns a system and method for evaluating textual data, such as chemical identifiers obtained from source documents, using a virtual N-dimensional array. The described system and method, in part, are directed to extracting from the source documents chemical identifiers and converting those chemical identifiers into coded forms. Further aspects are directed to plotting, or identifying plot coordinates, such as a 2D or 3D plot, of coded forms in a low dimensional space, in which the location of each coded form in the space is based on the similarity of each of coded forms to one another.

BACKGROUND OF THE INVENTION

Typically, text documents that are in the field of chemistry, such as patent applications, research reports, and other investigations, refer to chemicals using generic chemical formulas. These generic formulas are commonly used as stand-ins for a multiplicity of actual chemical formula that are encompassed by the generic formula. For example, a text document might reference a substituent, moiety, or other generic place holder that is a short hand for a number of possible atoms or molecules (e.g. a methyl, ethyl, or aryl group) the make up a particular formula.

Similarly, in other technical fields, a convention or nomenclature is sometimes used to represent a set of related subject matter, such as nucleotide sequences, amino acid sequences, and so on. For instance, adenine and thymine can be represented in a nucleotide sequence with a generic substitute, x.

Understanding the scope of the subject matter covered by, say, a generic formula or generalized representation, enables researchers, patent attorneys, and business persons to identify areas of further study, potential business strategies and intellectual property disputes. More particularly, identifying licensees, research partners, or infringements can be challenging when generic chemical names or other generic representations are used in patents and other documents, because the generic terminology can mask whether there is an overlap or opportunity relating to, say, a particular chemical formula or a particular nucleotide sequence that is of interest.

There are a number of analytical techniques to allow for searching a database for specific structural formulas or specific representational forms that are represented by a generic chemical formula or generalized representation. However, these solutions are usually time consuming and include manually identifying or drawing, in the case of chemical formula, the structural formula, and these fall short of providing an environment in which overlapping subject matter between documents can be identified. New chemical entities evaluate libraries of documents to extract usable information. Furthermore, it is known in the art to convert and manipulate chemical structures using computer analyses and algorithms. These techniques, let alone one in which new chemical entities can be identified which relate to a particular biological target or particular subject matter.

Therefore, what is needed is a system and method that provides a mechanism for generating from generic chemical identifiers one or more sets of queries representing the generic formula and searching a chemical database for specific compounds that match the queries in order to identify those entries in the database having overlapping subject matter with the generic chemical formula. Likewise, what is needed is a system and method that provides a mechanism for generating from generic representational data one or more queries representing the generic representational data and searching a database of representational data to identify those entries chemical identifiers in order to identify in the database that have overlapping subject matter with the generic representational data. What is further needed in the art is a system and method which can organize the identified documents in a virtual presentation in support of analytics upon the documents to reveal opportunities. The present invention addresses these and other needs.

Currently, in machine learning and statistics, one way to assess a similarity between, say, chemical entities represented by chemical identifiers such as chemical structure formulas, is to convert the chemical structure formula into a coded representation. It is also known to use analytic procedures to convert a symbolic representation (e.g., chemical identifier) of a molecule (e.g., chemical entity) into a useful number or value for the purpose of comparing, as one example, one chemical entity to another. For example a variety of descriptors is known and can be used in lieu of keybit binary representations in order to generate values that are useful in implementing certain embodiments of the invention. As non-limiting examples, known descriptors include 0D (i.e., constitutional descriptors), 1D (i.e., lists of structural fragments), 2D (i.e., graph variants), 3D (i.e., quantum-chemical descriptors), and/ or 4D (i.e., GRID).

When there are a large number of variables in the dataset, such as in multivariable datasets defined by the keysets mentioned above, dimensionality reduction techniques can be used to evaluate the datasets. These techniques can be used to reduce datasets to a few principal variables in order to more easily visualize the relationship between datasets. Techniques can be used to evaluate the datasets. These techniques can be used to reduce datasets to a few principal variables in order to more easily visualize the relationship between datasets. Node or diffusion mapping algorithms, for instance, can be used to embed high-dimensional data sets into, say, a Euclidean space. Using this technique, the coordinates of each data point in the Euclidean space are computed from the eigenvectors and eigenvalues (i.e., non-zero vectors or values that, when multiplied by a matrix, generate multiples of the vectors or values). Such mapping techniques are computationally inexpensive and are useful in reducing and displaying visually-complex multivariable datasets such as product reviews, internet traffic, and E-commerce reports.

The techniques discussed above are all appropriate for mapping chemical structures that are represented by respective datasets. Turning to the question of new chemical entity discovery, however, while there exist chemical compound discovery techniques that are useful in identifying novel chemical compounds, current systems are not able to generate additional compounds in the low-dimensional space.

One technique for compound discovery which is used in identifying therapeutic compounds is scaffold hopping. Scaffold-hopping is used to identify isofunctional molecular structures with significantly different molecular backbones. Some types of scaffold-hopping include, but are not limited to, heterocycle replacements, ring opening or closure, peptidomimetics and topology-based hopping techniques. Other bioisosteric replacement techniques are also useful in predicting and evaluating new chemical compounds.

In short, current analysis systems are configured to process large variable data sets and present lower dimensional (e.g., 2- or 3-dimensions) visualizations to a user. Yet these systems are not configured to generate additional data relating to a chemical that might be further included or missing from the data set, and are entirely unable to identify absent chemical structures that conform to a reduced dimensional space.

Therefore, what is needed in the art is a system and a method which can construct an artificial environment which is trained around a particular biologic target or subject matter, such as a virtual manifold or a virtual array of nodes, from which common chemical features can be identified, transformed into new coded forms and inserted into the artificial environment for determining whether its placement within the artificial environment fits at least one prescribed criterion. What is further needed in the art is a system and method for predicting and generating chemical identifiers that describe new chemical entities not currently found within the source documents used to generate the artificial environment, yet which fill gaps in the artificial environment. The present invention addresses these and other needs.

SUMMARY OF THE INVENTION

The present invention is directed to generating a collection of queries representing a generic chemical formula by building up the potential values of the side chains and backbones and searching a database for entries that contain a combination of the unique values for each of the backbones and side chains. The positive search results are used to identify and analyze the relationships between the returned database entries and the generic chemical formula.

More specifically, the present invention is directed to a computer-implemented method for analyzing a generic chemical formula, wherein the generic chemical formula comprises at least a plurality of moiety variables, each moiety variable having a defined set of possible values, wherein each unique combination of the possible values defines a chemical identifier. These unique combinations, together with any invariant fragment, are instantiations of the moiety variables that correspond to the generic chemical formula. The invariant fragment of a given generic chemical formula can comprise, for instance, a core or scaffold or backbone, including, by way of example and not limitation, any phenyl or other homocycle group, an amide structure, or a heterocycle group.

The method includes assigning each moiety variable a value array; extrapolating to each value array, within a memory of a computer using a query generation module comprising code executing in a processor, at least a portion of the set of values associated with the given moiety variable (e.g., known values), the set of possible values including one or more values (e.g., known values). A query is defined for use in searching a database using code executing in the processor. The query includes, for at least one moiety variable, either the contents of the value array or a reference to the contents of the value array. The query is applied to the database, using a query comparison module comprising code executing in the processor, wherein the database comprises a collection of unique chemical identifiers. A results module configured as code executing in the processor within the memory of the computer generates a list of database entries encompassed by the query that match within at least one prescribed criterion. A visual indication is provided identifying each database entry encompassed by the query, wherein the visual indication further identifies the specific values for each moiety variable found in the list of matching database entries.

More particularly, one method in accordance with an aspect of the invention includes the use of a conversion module, to convert at least a portion of the chemical identifiers that correspond to the generic chemical formula into respective coded representations. The coded representations can be numerical forms, or another coded form that is specific to a particular database.

In one arrangement, the database is a collection of indexed entries, each entry containing a chemical identifier. In an alternative arrangement, the each database entry is linked to a source document indicating where that chemical compound was described in a publicly accessible document. Thus, the method includes identifying those publicly accessible documents that contain chemical formulas that match one of more of the search queries. These overlapping subject matter disclosure documents are presented to a user as a visualization of the results of the search, or, used as input to a multi-dimensional mapping system designed to generate a 2-dimensional map of the similarity of the chemical formulas found in the database and the formula represented by the generic chemical formula.

The present invention, according to one aspect, is directed to a computer-implemented method for extracting representational data relevant to a particular subject matter, such as chemical entities, from source documents which discuss the subject matter, and populating an n-dimensional manifold, such as an n-dimensional node array, with coded representations of the representational data (e.g. chemical identifiers, nucleotide sequences, textual fingerprint data, or a hybrid of the foregoing). The method comprises generating a virtual n-dimensional manifold within a memory of a computer using a manifold-generator module which comprises code executing in a processor and placing, using a placement module which comprises code executing in the processor, each of the coded representations at a location, such as a particular node within the manifold, using an unsupervised learning algorithm.

Optionally, the method as above, according to a further aspect, can include the additional step of adjusting a placement of each coded form within the virtual manifold in the memory using an adjustment module which implements a neural network algorithm using code executing in the processor.

In a further arrangement, the method also includes predicting new representational data that will occupy the manifold, such as a particular node of the array when placed within the array. In an example where the representational data are chemical identifiers, the further steps include comparing at least one chemical feature ("CF") corresponding to the coded form contained within at least a first array node to at least one CF corresponding to the coded form contained in at least a second array node using a CF module which comprises code executing in the processor, the first and second nodes each sharing a border with each other or a third node in the virtual node array. The method according to this aspect includes identifying common CFs between the first and second array nodes using a commonality module which comprises code executing in the processor, and generating at least one new coded form based on combinations of the identified common CFs which, when inserted into the virtual node array, results in a placement in the first or second node or within a third adjacent node using a coded form generator module which comprises code executing in the processor. The method outputs a chemical identifier corresponding to the new coded form and augments a data store of chemical entities for the user.

In another aspect, the present invention can be embodied by a computer-implemented system utilizing a processor configured by a plurality of code modules executing therein to extract or select from a collection of target documents a plurality of a generic chemical formulas, each generic formula having at least one variable, that variable having a set range of potential chemical forms, and to generate a query or collection of queries that represents each of those generic formulas. These queries are used to search the same database such that positive matches returned using both queries provide an indication of subject matter common to multiple target documents.

In another aspect, the present invention can be embodied by a computer-implemented system utilizing a processor configured by a plurality of code modules executing therein to output representational data, such as chemical identifiers and synthesis strategies relating thereto, that is not present in a data store of representational data. In particular, the system includes instruction code in the form of software modules that configures the processor to obtain, from a collection of source documents pertaining to a particular subject matter, the representational data described therein and convert the representational data into a high-dimensional coded form. The system according to this aspect can further comprise code that generates a virtual n-dimensional manifold within a memory of a computer using a manifold-generator module and which places, using a placement module, each of the coded representations at a location, such as a particular node within the node array, using an unsupervised learning algorithm.

In a further aspect, the present invention utilizes natural language processing techniques to generate queries from target documents in regard to generic representations of scientific information, without limitation to a particular field such as chemistry. In this embodiment, the present invention generates queries that provide a generic representation of the subject matter described in a patent or a patent document. The queries can produce results the same as in other implementations of the invention for visualization or other purposes.

A comparison module is included or utilized to compare, with a processor, a first plotted coded form at a first coordinate location within the virtual n-dimensional manifold, with a second plotted coded form at a second coordinate location in the virtual n-dimensional manifold. In one embodiment, this comparison module is utilized when at least one coordinate location between the first coded form and the second coded form lacks a plotted coded form, and in another embodiment can be used when at least one coordinate location adjacent the first and second coded forms is vacant. The comparison of coded forms is used to identify any common features shared by the first and second coded forms, e.g., common chemical features or sequence similarities. The system further includes a generation module utilized to execute code on a processor in order to generate at least one new coded form based on combinations of common features of the entities corresponding to the coded form located at the first coordinate location and the coded form located at the second coordinate location of the virtual n-dimensional manifold.

Optionally, the generation module described above is further configured to generate a synthesis strategy for synthesizing representational data described by the at least one new coded form using a standard synthesis strategy, such as retrosynthetic analysis.

In another aspect, the present invention can be embodied in a computer-implemented system utilizing a processor configured by a plurality of code modules executing therein to output a DNA, RNA, amino acid or other sequence data and synthesis strategies relating thereto, corresponding to biomedical or biopharmaceutical products not present a data store. In particular, the system includes instruction code in the form of software modules that configures the processor to obtain from a collection of source documents pertaining to a particular subject matter the representational data described therein and to convert each instance of representational data found in the accessed documents into a high-dimensional coded form. These high-dimensional coded forms are plotted to a virtual n-dimensional space or manifold, such as an n-dimensional node array. A comparison module is included or utilized to compare, with a processor, a first plotted coded form at a first coordinate location within the virtual n-dimensional manifold, with a second plotted coded form at a second coordinate location in the virtual n-dimensional manifold. In one embodiment, this comparison module is utilized when at least one coordinate location between the first coded and form the second coded form lacks a plotted coded form, and in another embodiment can be used when at least one coordinate location adjacent the first and second coded forms is vacant. This comparison is used to identify any common features shared by the first and second plotted coded forms. The system further includes a generation module utilized to execute code on a processor in order to generate at least one new coded form based on combinations of common features of the entities corresponding to the coded form located at the first coordinate location and the second coordinate location of the virtual n-dimensional manifold.

The present invention, in further aspects, can include steps or system components to synthesize a compound in which the chemical formula for the compound is determined according to a new chemical entity discovery process as described herein.

The present invention, in still further aspects, can comprise a compound described by a new chemical entity identifier that has been generated according to the steps of the process provided and system described herein, wherein the compound is synthesized according to a synthesis strategy generated as described hereinbelow.

These and other features and aspects will be understood from the discussion below of certain embodiments of the invention.

BRIEF DESCRIPTION OF THE DRAWINGS

FIGS. 5A, 5B, 5C and 5D are depictions of the visualization component of the described system and method.

FIG. 8 is an illustrated diagram of the elements of the system of an embodiment of the present invention.

DETAILED DESCRIPTION OF CERTAIN EMBODIMENTS OF THE INVENTION

Figure 1:
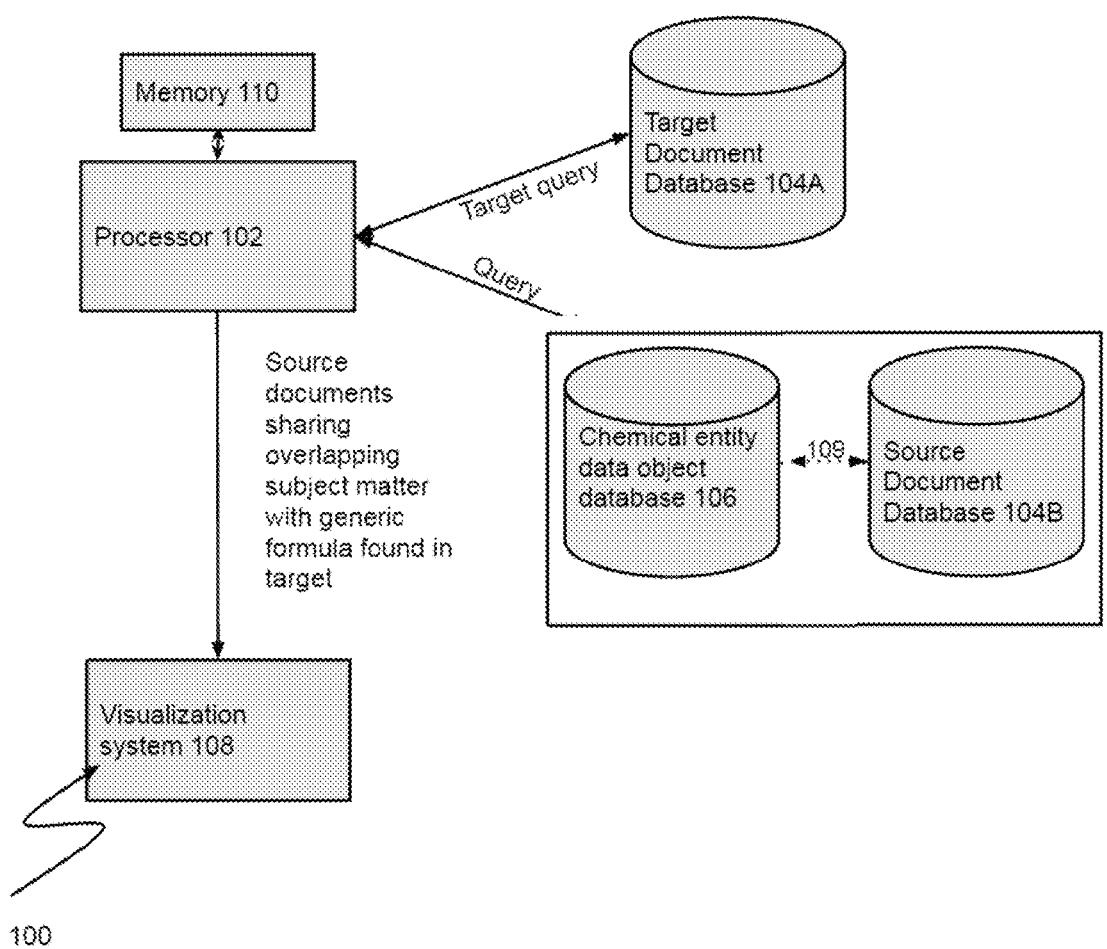
FIG. 1 is an overview block diagram detailing the arrangement of elements of the system described herein in accordance with one embodiment of the invention.

By way of overview and introduction, the present invention concerns a computer implemented system and method for identifying overlapping subject matter in several contexts. In one implementation, the invention identifies overlapping subject matter between a generic chemical formula found in a target document and chemical formulas found in a chemical database. In another implementation, the present invention concerns identifying subject matter common to a plurality of target documents. For example, one implementation of the present invention concerns generating a collection of queries representing the generic formula described in a target document. The generated collection of queries are used to search a chemical compound database of known chemical formulas and generate a virtual landscape to evaluate the relationship between the compounds described by the generic formula generated formula.

U.S. patent application Ser. No. 14/795,218 (now U.S. Pat. No. 10,013,467), filed on even date herewith, entitled "System And Method For Evaluating Textual Data Using And Applying A Virtual Landscape" naming inventors Kevin Brown and Kevin Brogle, which is hereby incorporated by reference as if set forth in its entirety herein, describes the generation of a virtual landscape showing the relationship between documents detailing a particular biological target of interest. The virtual landscape generated in that application includes, among other things, the universe of documents stored in a database that make reference to a particular biological target (e.g. sodium channel inhibitors).

The present disclosure identifies the relationship between chemical structures, amino acids, or textual data that can be described using a common generic formula. The landscape generated herein can be understood, in one respect, as being a focused view of the landscape that can be provided in the aforementioned application. That is to say, the subject matter of the present landscape encompasses the universe of chemical compounds described by the generic formula, not the biological target. Thus, if the generic formula concerns sodium channel inhibitors, the landscape provided in the present invention will be a landscape of sodium channel inhibitors encompassed by the generic formula. The same landscape will, therefore, omit dissimilar structures not encompassed by the generic formula, even if the structures are sodium channel inhibitors, whereas the aforementioned co-pending application can include dissimilar structures that make reference to the same biological target.

The queries generated are used to search the entries of a general or custom database of chemical identifiers to determine if a specific formula disclosed within the database is described by the generic formula. Thus, in accordance with the invention, disclosed structures can be identified and depicted in the landscape. Furthermore, by providing a landscape with gridlines configured to represent the respective distances between disclosed chemical structures, the artificial landscape reveals and provides a workspace to explore opportunities for research, development, licensing and enforcement.

In a more particular implementation, the system and method is configured to convert the generated chemical formulas to a query format through the use of an algorithm to match the chemical name or other chemical nomenclature obtained from the target document describing possible side chain and backbone variables. The conversion and generation algorithm takes different forms of chemical nomenclature and converts each into a common format that is suitable for further processing or storage. However, in one arrangement, the algorithm is used to convert the chemical nomenclature into a format that is suitable for searching a chemical structure database and predicting new chemical entities based on the analysis of source documents, such as patent documents. The system and method are configured to carry out a series of steps, implemented as instructions executed by a processor of a computer, in order to generate a virtual space from which new chemical entities are predicted and output as one or more new chemical identifiers corresponding to chemical entities not disclosed in the source documents.

Throughout the following discussion, the American spelling of the singular "formula" and plural "formulas" is used instead of the British spelling convention "formulae/formula."

As used herein, "representational identifier" means a format or nomenclature utilized as a representation of particular subject matter, such as nucleotide sequences, amino acid sequences, textual summaries or syntactic fingerprints, and/or chemical entities.

As used herein, "chemical entities" comprise chemical compounds, substances and non-stoichiometric compounds.

Also as used herein, "chemical identifiers" means any schema used to identify a specific chemical entity. For example, chemical formulas, structural formulas, chemical names derived from any chemical nomenclature, or trivial names all can be utilized in the systems and methods herein. In one particular arrangement, the chemical identifiers identify an opioid agonist (e.g. hydrocodone, morphine, hydromorphone, oxycodone, codeine, levorphanol, meperidine, methadone, oxymorphone, buprenorphine, fentanyl and derivatives thereof, dipipanone, heroin, tramadol, etorphine, dihydroetorphine, butorphanol, levorphanol). In a further arrangement, the chemical identifier identifies molecules that interact with specific G-protein coupled receptors, tyrosine kinase linked receptors, guanylate-cyclase linked receptors, nuclear steroid receptors, membrane bound steroid receptors, ligand-gated ion channel receptors or adhesion molecules.

As used herein, "biologic entities" comprise macromolecular products or biopolymers, such as but not limited to, nucleic molecules or residues, carbohydrates, fatty acids, peptides, monoclonal antibodies, polypeptides, proteins, natural and non-natural amino acids, and portions or fragments thereof.

Also as used herein, "biologic identifiers" means any schema used to identify a specific biologic entity or any portion thereof. For example a biologic identifier also means a specific peptide, protein or nucleic acid or any amino acid, DNA or RNA sequences, or portions thereof. Furthermore, biologic identifiers can also mean any convention used to identify specific formulas, structures, folding diagrams, names derived from any nomenclature, or trivial names associated with a biologic entity.

As used herein, a "coded form" is a multivariable data representation of a particular set of information relating to the structural, sequential, physical and/or binding properties of a chemical, biologic, or textual entity represented by a chemical identifier, a biologic identifier, or words or characters represented by a n-gram sequence. By coding such properties, an assessment of the similarities that exist among and between different chemical, biological, or textual identifiers can be made, including automated assessments.

As used herein, "similar" is meant to describe chemical entities having substantial overlap in chemical structure, physical properties, or overlapping pharmacological properties, and in regard to chemical and other subject matter, "similarity" can be discerned based on a distance metric calculated within a virtual n-dimensional space, as will be understood from the following discussion.

Overview

FIG. 1 illustrates a computer system 100 configured to carry out the transformation of the subject matter described by a patent claim into a set of queries that can be used to search a database for the purpose of identifying entities practicing the patent claim. For ease of explanation, the following implementations are directed to transforming a generic formula found in a patent claim into a set of queries used to search a database of chemical identifiers. In one arrangement, the queries are sets or collections of potential values for the backbone and sidechains of the generic formula.

However, in alternative arrangements, the system is configurable to extract, transform and analyze non-chemical data from patent documents.

In part, the present invention concerns generating datasets which associate the extracted chemical identifiers, the coded forms corresponding to these extracted identifiers, and links to the originating source documents. By maintaining an association between these datasets, systems and methods in accordance with embodiments of the present invention can derive relationships between the datasets based on the chemical identifiers, rather than in view of their coded forms. These relationships enhance the principal function of generating potential new chemical entities by managing and utilizing source document data based on the underlying relationships between data extracted from the source documents. The computer system includes one or more hardware processors 102 configured to access database 104A containing one or more target documents. The processor 102 generates a collection of queries that describe at least a portion of the generic chemical formula obtained or extracted from the target database 104A and searches a chemical formula database 106 for matches to the query. In a particular arrangement, the processors 102 are further configured to access a source document database 104B containing one or more references to specific chemical identifiers found in the chemical formula database 106. Each stored source document in database 104B contains at least information relating to a particular biological target of interest, such as small molecules (e.g., sodium channel inhibitors), bibliographic information and other information generally describing chemical structures or formulas of compounds that can interact with the biological target.

Upon carrying out the steps described herein, through code executing within the memory of the processor(s) 102, as may be organized into one or more modules, or firmware or hard-wired circuitry, in one implementation, the processor 102 sends an indication of the results of the search to the visualization or output device 108. In a particularly advantageous result, A search performed in a conventional manner on the database 104, including possibly several databases of documents, yields a universe of documents that relate in one manner or another to the biological target of interest.

In one embodiment, the computer system 100 is illustrated in FIG. 1 and includes a computer (not shown) which has a hardware processor 102 configured to access a database 104 of stored source documents. Each stored source document contains at least information relating to a particular subject matter. In one instance the subject matter is a biological target of interest (e.g., sodium channel inhibitors,), and information describing chemical structures, formulae, antigens, amino acid sequences, or nucleotide sequences used to interact with, or related to, the biological target.

Upon carrying out the steps described herein, through code executing within the memory of the processor(s) 102, as may be organized into one or more modules, or firmware or hard-wired circuitry, in one implementation, the processor 102 sends an indication of the results of the search to the visualization or output device 108. In a particularly advantageous result, A search performed in a conventional manner on the database 104, including possibly several databases of documents, yields a universe of documents that relate in one manner or another to the biological target of interest.

In a particular embodiment of the present system, the source documents are published patent documents, including patent applications and patents, available through the United States Patent and Trademark Office, optionally from foreign patent offices and from various commercial patent databases. Other collections of non-patent documents are suitable for use with the system and method, such as, by way of example and not limitation, technical and scientific journals, research compendiums, and other documents containing information relating to chemical compounds, any or all of which can be included in the database 104. Particular advantages result, however, when the source documents include published patent documents because one effect of the predictive engine described herein is the potential to identify novel and inventive chemical or biologic formula, sequences or structures, including ones not documented in the patent literature in connection with a particular biological target.

As illustrated in the high-level block diagram of FIG. 1, the processor 102 is configured by code stored in its memory 110 to extract data from the source document database 104 and generate a collection of representational data objects that preserves the relationship between the representational data and the source document. While the present discussion is in relation to the processor 102 and the memory 110, the processor can include multiple cores, or can be embodied as a plurality of processors, each being provided with code from a respective memory, as may be implemented in a distributed computer implementation of the invention.

In one arrangement, representational data objects are amino acid sequences. In an alternative embodiment, the representational data are chemical entity identifiers. However, for ease of discussion, the following example will use chemical identifiers to illustrate the implementation of the described embodiments.

Thus, for example, chemical entity data objects can be stored in a representational data object database 106. When evaluating chemical compounds, the representational data object database is a chemical entity data object database. Alternatively, when evaluating biologic entities or identifiers, the representational data object database 106 is a biologic data object database. In an alternative context the representational data object database is a textual data object database. In one embodiment, the processor 102 executes software modules stored in the memory 110 which configure the processor to access the database and generate predictive or analytic outputs based on the contents of the chemical entity data object database 106 and based upon algorithmic logic discussed in this specification. Through the use of code modules stored in the memory 110, the processor 102 can provide a visualization via a visualization system 108 of a virtual target landscape which is constructed and exists in the computer implementation in order to present locations in the landscape at which new or predicted biological, textual or chemical entities (BCEs, TCEs or NCEs) are predicted to reside. Such BCEs, TCEs or NCEs are not described within the universe of source documents that gave rise to the virtual landscape for the particular biological target of interest, and only a portion of potential BCEs, TCEs or NCEs would be of interest, such as those BCEs, TCEs or NCEs that occupy prescribed placements or locations within the constructed landscape.

Based on a selection of specific chemical entities from among the entities in the representational data object database 106, the modules configure the processor with code that executes therein to generate or "propose" new chemical, biologic or textual entities not currently described in the source document database or the representational data object database 106, but which are similar to a particular selection as a function of location within the virtual landscape (e.g., a visualization presented in a low-dimensional node array).

In an arrangement based on the selection of specific biologic entities from among the biologic entities in the database 106, the modules configure the processor with code that executes therein to generate or "propose" new biologic entities not currently described in the source document database or the biologic entity object database, but which are similar to a particular selection as a function of location within the virtual landscape (e.g., a visualization presented in a low-dimensional node array).

As used herein, "similar" is meant to describe chemical, biologic or textual entities having substantial overlap in chemical structure, sequences, domains, features and physical properties. The selection and generation can be made by the user alone, such as by interaction with the virtual landscape to guide further processing to identify new representational data with a particular placement within the landscape, programmatically, or through a combination of the two according to a pre-defined rule set or instructions. In one embodiment, as will be described in more detail below, a user can review a first visualization of chemical entities discussed in a set of selected source documents, namely, source documents that relate to a certain biological target, and select one or more chemical entities identified from that set of documents for further analysis. A range of similarities that exist between the predicted chemical forms and the chemical forms that have been selected in this way can be displayed to a user through the embodiment of the visualization system 108. Alternatively, the ranges of similarities as determined by the system are presented in a different manner. Regardless of the approach taken, the predicted and selected chemical forms can be stored in a storage device for future access or reference.

The processor 102 is configured to perform a series of discrete steps to access, analyze and generate outputs relating to the data in a database of unique representational identifiers. The processing tasks can be distributed among several processors 102, and among several machines having the processors 102, in a particular implementation. In one embodiment, the database is a chemical database 106, and the processor performs such steps as describing queries that represent at least a portion of a generic formula and searching the contents of the chemical database 106 for matches to the query.

The processor 102 is configured to perform a series of discrete steps to access, analyze and generate outputs relating to the data in the representational data object database 106 as described. As will be apparent from the accompanying discussion of methods in accordance with aspects of the invention, prediction and identification of new chemical entities, or any other representational data, is performed in regard to a virtual landscape defined by a particular algorithmic approach and the identification includes fitting the newly identified chemical entity or other representational data into that landscape, regardless of whether there is a visualization of the landscape or not.

Discussion of the Principal Modules and Certain Methodologies

Figure 2:
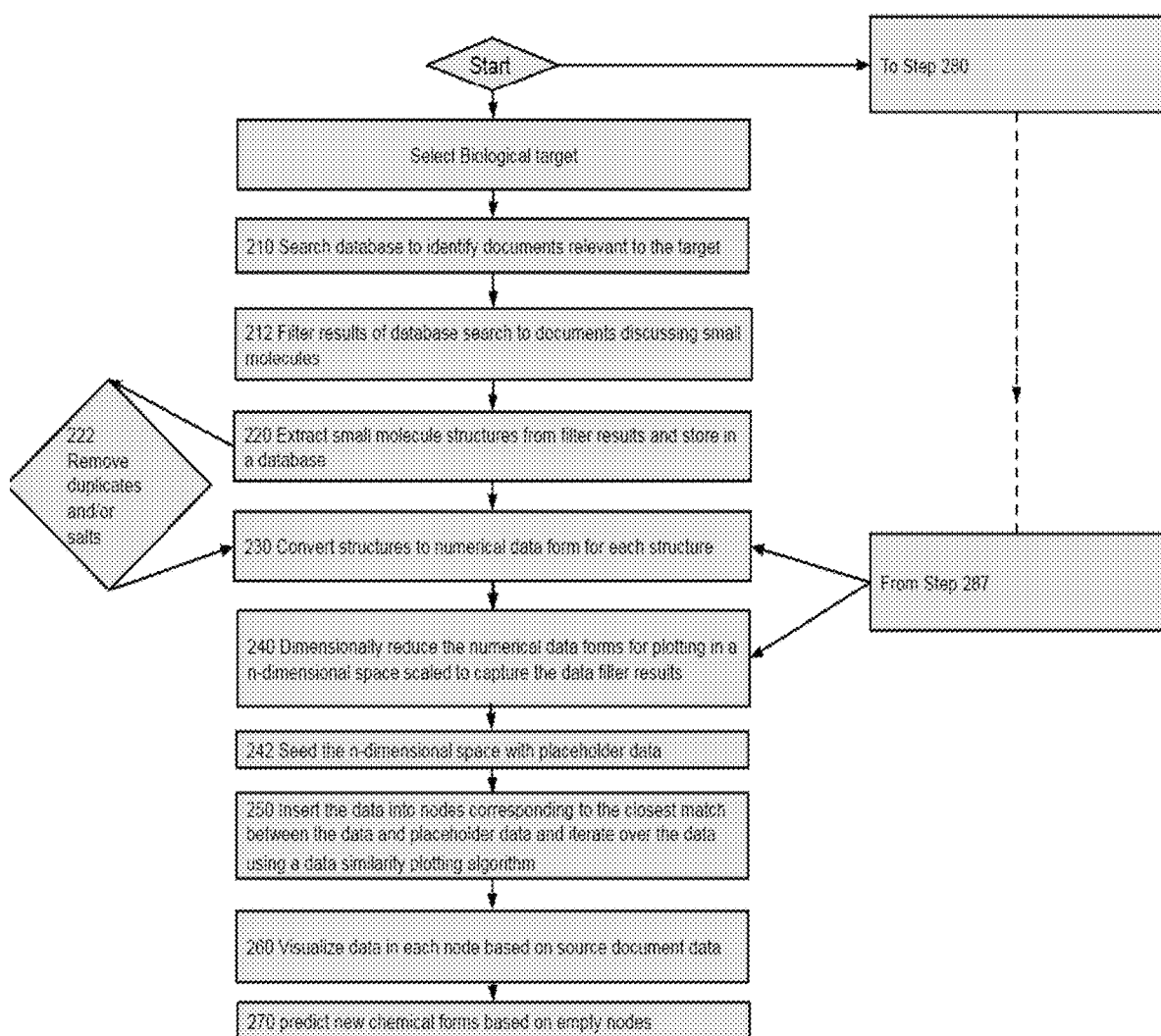
FIG. 2A is a flow diagram detailing the steps of an embodiment of the method applied to chemical entities as described herein.
FIG. 2B is a flow diagram detailing the steps of an embodiment of the method applied to biologics as described herein.
Figure 2A:
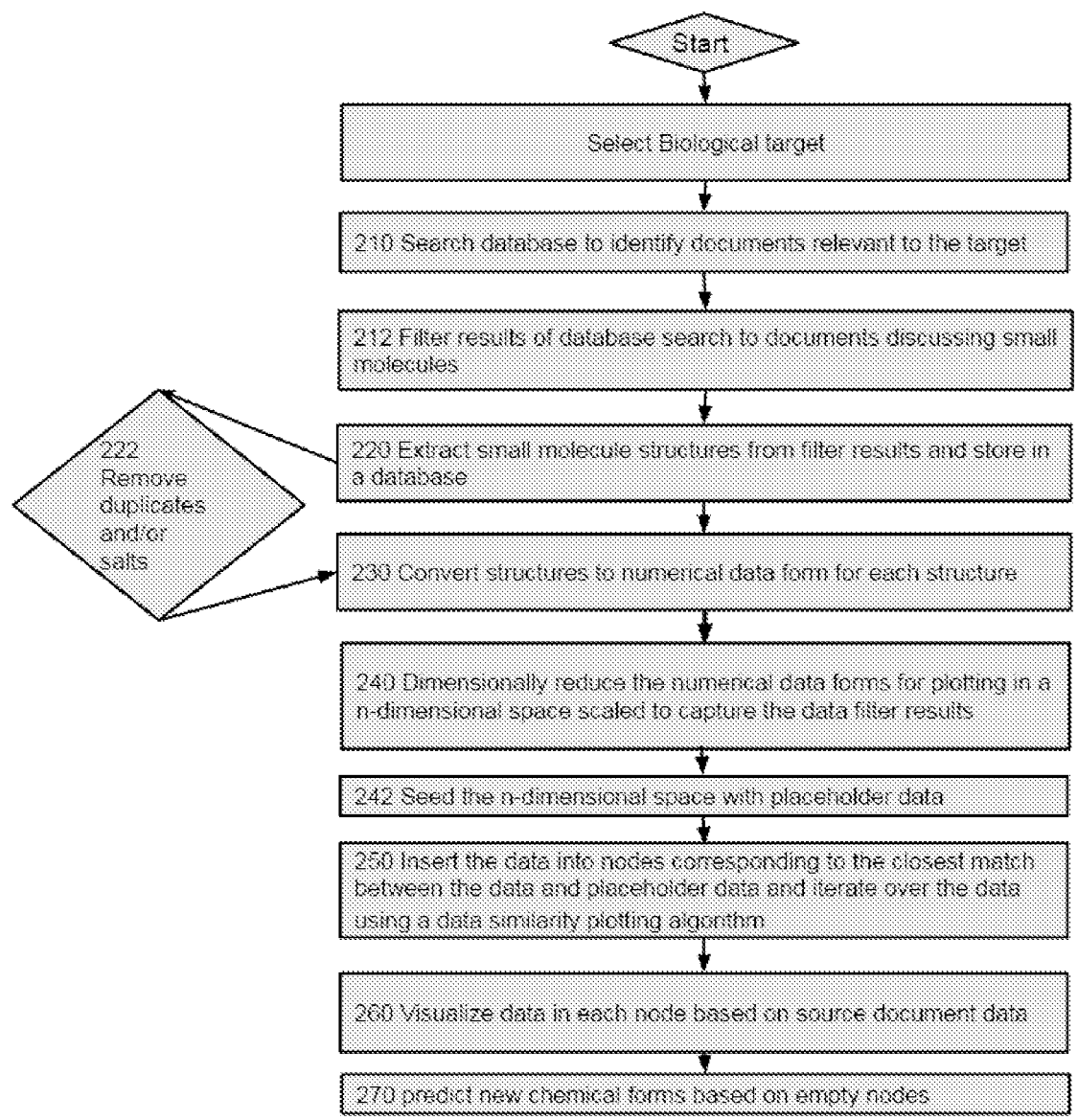

FIGS. 2A detail particular work-flows in accordance with aspects of the invention, in which the subject matter of interest is a biological target and in which new chemical entities are to be located. When the discussion permits, additional examples are included. Likewise, FIG. 2B details the same workflow as in FIG. 2A but is directed to locating new biologic entities.

Figure 2B:
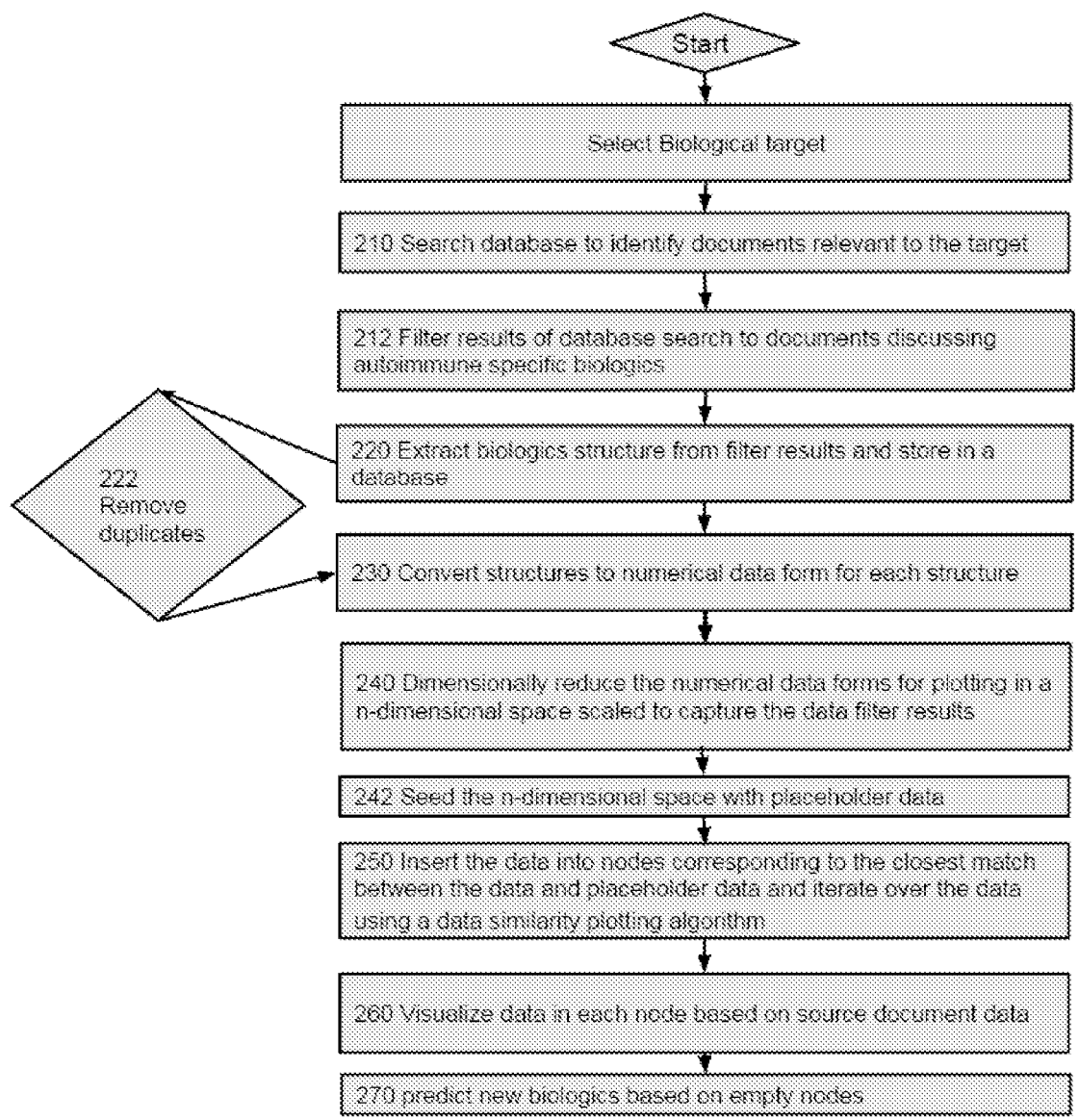
Figure 2C:
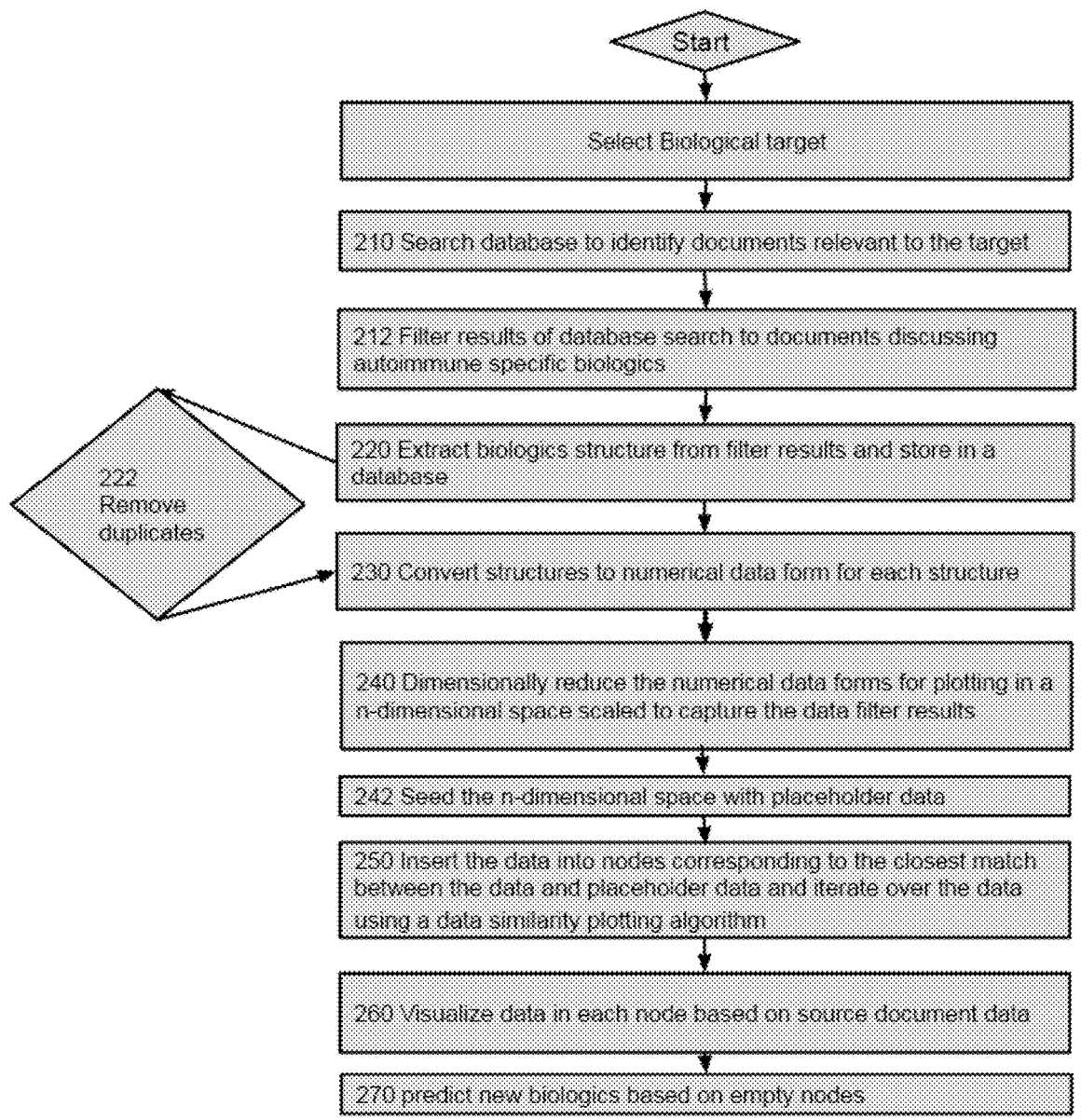
Figure 3:
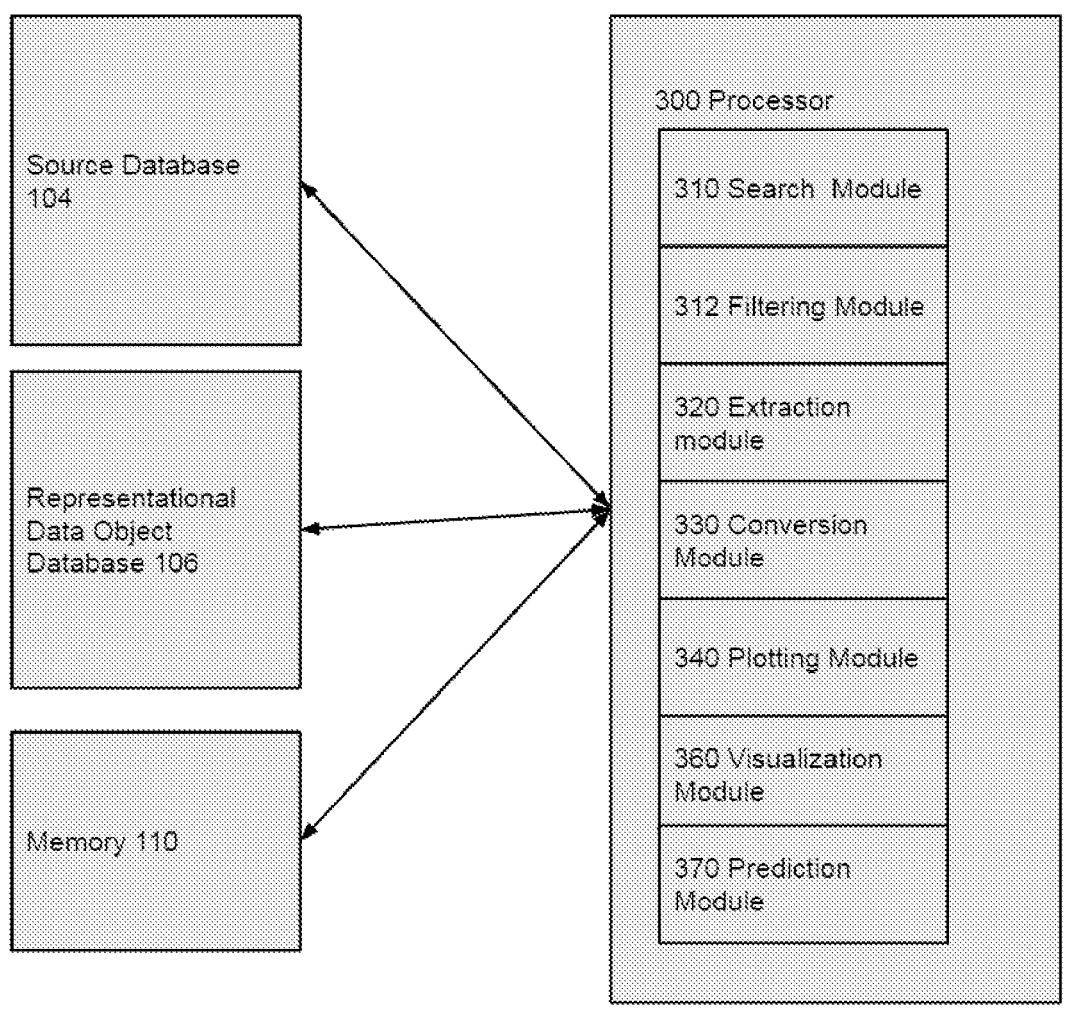
FIG. 3 is a block diagram of an example system in accordance with an embodiment of the present invention.

The steps shown in FIGS. 2A-B can be carried out by code executing within the memory of the processor 102, as may be organized into one or more modules, or can comprise firmware or hard-wired circuitry. For simplicity of discussion, the code is described in the form of modules that are executed within the processor 102 and which are each organized to configure the processor 102 to perform specific functions. The block diagram of FIG. 3 provides an exemplary description of the modules that cooperate with the memory 110 and processor 102 to implement the steps outlined in FIGS. 2A-B, and are shown for ease of illustration as all being associated with a single processor 102 and memory 110. As noted previously, the processor 102 can comprise a plurality of cores or discrete processors, each with a respective memory, which collectively implement the functionality described below, together with associated communication of data therebetween.

Target Documents

A target document as used herein is a document containing one or more generic representational identifiers. One or more target documents are stored in a target database 104A for use with the present system and method. In a particular embodiment, the target document database 104A contains, or provides links to, at least one target document describing a generic formula, textual data or other data found within a patent document. Other suitable target documents, by way of non-limiting example, such as technical and scientific research reports or scientific findings, research compendiums, white papers, technical proposals, and other documents containing information relating to generic or representational data (e.g., chemical formula, nucleotide sequences, textual or syntactic fingerprints) that describe a number of potential outcomes relative to the representational data (e.g., chemical formula encompassed by the generic formula, or nucleotide sequences described by a generic sequence listing) are suitable for use with the present system and method. Alternatively or in addition, the target document describes a composition, apparatus, process, or manufacture. As described in more detail below, the target document(s) contained within the target document database 104A provides the generic representational identifier used to search a collection of specific representational identifiers.

The target database 104A is locally accessible by processor 102. In the alternative, the target database 104A is a remote database or server accessed through a network (e.g., a LAN, WAN, or the internet). In the event that the processor 102 is configured to access a remote database, the processor includes the necessary hardware and software (e.g., TCP/IP protocols and network interface hardware) necessary to establish a connection to a remote data storage location and receive data sent by the same.

Source Documents

As used herein, source documents include any entry in a database or documents containing representational identifiers and used to identify the scope of the generic representational identifier. In one arrangement, the source documents are obtained by executing searches for subject matter of interest on a document database (e.g. a patent database) and storing either a reference to the documents returned in the search results or a copy of the actual document to a source document database 104B.

With reference now to FIGS. 2A-B and 3, the prediction and new chemical entity generation system is initiated and implemented by at least one search module 310 which comprises code executing in the processor 102 to access and search the records in the source document database 104 according to step 210.

U.S. patent application Ser. No. 14/795,375, (now U.S. Pat. No. 10,372,713), filed on even date herewith, entitled "Chemical Formula Extrapolation And Query Building To Identify Source Documents Referencing Relevant Chemical Formula Moieties" naming inventors Kevin Brown and Kevin Brogle, which is hereby incorporated by reference as if set forth in its entirety herein, describes a system and method that can be used for constructing suitable queries. In brief, a set of specific representational identifiers that are represented or covered by a generic representational identifier found in, say, a target document, can be extrapolated and queries can be constructed and performed on a corpus of source documents for purposes of comparison of the members of the extrapolated set of specific representational identifiers to a database of known representational data. By matching known representational data in this way, any overlap between the generic representational data and specific instances of the generic representational identifier within the source documents is determined, and in specific implementations, the system and method reduces the scope of the generic representational identifier such that the reduced scope generic representational identifier encompasses only novel specific representational identifiers.

The database search step 210 executes to retrieve documents that discuss a subject matter of interest, such as a biological target of interest, from among the source documents. The records that reference the target of interest can be located, for instance, using text searching of the source documents or searching of an index of the source documents. As will be appreciated, the source document database 104 can comprise a single repository of records or can comprise an aggregation of data stores. In one example, the system is configured to connect through the Internet to a remote document database. In this embodiment, the system is equipped with modules capable of configuring the processor to query remote databases and parse the results. In one embodiment a network interface card (NIC) is configured to communicate with the processor 102 in order to establish a connection to an external network. In another embodiment, a wireless adapter is used to communicate with the processor 102.

In a further example, the search module 310 includes code that executes so as to configure the processor 102 to search the applicable database(s) with defined search parameters such as a particular biological target of interest. Additionally, the search module 310 can include further code, as part of a single module or which may comprise sub-modules, which configure the processor 102 to return only those search results that match specific criteria. One search criterion can be the presence of chemical formulas or structures suitable for conversion into coded forms. A non-exhaustive list of search parameters that can augment or be run in addition to a search concerning a biological target of interest or other subject matter of interest includes: a publication date, inventor name, assignee name, country of filing, language, and other parameters typically included on a cover page of a printed patent, published patent application, or in a conventional patent document database.

The collection of source documents, in one arrangement, is stored in the source document database 104B and used to identify chemical identifiers of interest in the chemical entity database 106. In a further embodiment, the results from the database query of step 210 can be filtered using a filtering module 312 which can comprise code executing in the processor 102 in order to perform a filtering step 212. The filtering module 312 in one particular embodiment configures the processor to only access those source documents which include in their discussion a particular sub-set of the biological target of interest. In FIG. 2A, the filtering module 312 can configure the processor to execute a filtering step in which the results of a database query are filtered to identify those documents which relate to sodium channel inhibitors or other small molecule compounds. In FIG. 2B the filtering module 312 can configure the processor to identify those documents relating to an immune-mediated inflammatory disease. The results of this step and other steps can be managed within a memory of the computer, with data moved in and out of a non-transitory memory or stored elsewhere, as required.

In one embodiment, the results of the filtering step 212 are stored in the chemical or biologic entity data object database 106. In an alternative embodiment, the search module 310 configures the processor 102 to store the results of the query in a non-transitory memory or an external, non-volatile storage device, either of which is accessible to the processor 102.

Once the data from the source documents is stored in a storage location, it is made available to the processor 102 for analysis. In one embodiment of the system, the analysis of the data includes the use of an extraction module 320. The extraction module 320 can comprise code (more generally, "software") that configures the processor to perform an extraction step 220. The extraction step 220 causes the processor to obtain, from each source document, at least one specific chemical or biologic identifier found in the source document. For instance, the extraction module can perform a text parsing function that identifies candidates for extraction with reference to a rules base. For example, the rules base can instruct the text parsing function to parse prefixes, subscript and superscript components of a chemical name according to a pre-determined nomenclature schema.

In a particular arrangement, the extraction module is configured to extract alpha-blockers, beta-blockers, calcium and other ion channel inhibitors, opioids, and combinations or variants thereof. For example, the extraction module 320 is configured to extract from a source document one or more "true" alkaloids (e.g. atropine, nicotine, and morphine), alkaloids containing terpene (e.g., evonine) or peptide fragments (e.g. ergotamine) coniine and coniceine, protoalkaloids (e.g. mescaline, adrenaline and ephedrine), polyamine alkaloids, peptide and cyclopeptide alkaloids and pseudalkaloids.

Representational Identifier Database

The chemical entity database 106 can comprise a table, index, or other searchable collection of specific chemical entities. The described queries are used to search the contents of the database to identify those entries in the database having overlapping subject matter with the generic formula.

One configuration of the described system utilizes the source documents stored in the source document database 104B to identify representational identifiers, e.g., chemical identifiers of interest, by extracting each chemical identifier found in the source documents and saving it to the chemical entity database 106.

However, in an alternative arrangement, the representational identifier database 106 can comprise a commercial chemical entity database or a custom database having a pre-existing a collection of chemical entities. In a further implementation, the chemical identifiers indexed in the chemical entity database 106 also include a link to a document from which the chemical identifier was first identified and includes associated bibliographic information. In this arrangement, as indicated by feature 109, the entries in the source document database 104B are used, not to populate the chemical entity database, but to filter, using filtering module 312, the database entries to only those chemical entities described in one or more of the source documents in the source document database 104B.

In one embodiment, the database 106 is a chemical database or collection of chemical databases that contains multiple descriptors for the same chemical entity. For example, the chemical database can be a digital database that represents chemical structures as connection tables, adjacency matrices, lists with additional information on bond (edges) and atom attributes (nodes), and other data formats, file or data conventions, such as MDL Molfile, PDB, and CML formatted data. In one particular example, the chemical entity database 106 is a SDF file database, such as the type used by the ISIS BASE software program provided by BIOVIA. Alternatively, the chemical structures are stored in linear string notation based on depth first or breadth first traversal using formats such as SMILES/SMARTS, SLN, WLN and/or InChI. Those skilled in the art will appreciate that any database of chemical structures that allow representation of stereochemical differences and charges as well as special kinds of bonding such as those seen in organometallic compounds are suitable for use with the forgoing. Likewise, any database that allows for sub-structure searching of the chemical structures such as but not limited to using subgraph isomorphism (monomorphism) also can be used.

In an arrangement in which the target document discloses non-chemical information, the chemical entity database 106 contains a collection of nucleotide and/or amino acid sequences, word, token, text and phrase data relating to the subject matter of interest and is correlated to source documents from which such word, text, tokens or phrase data originated. In yet a further arrangement, the target document discloses biological data, such as nucleotide or amino acid sequences.

Obtaining Generic Representational Data from a Target Document

In order to analyze the generic formula for subject matter overlap or similarity with the formula described in the chemical database 106 or source documents, the generic formula is first transformed into a computationally useful form. The generation of these possibilities, specifically how the various combinations of side-chains and backbones are be combined, is determined programmatically according to a pre-defined rule set or instructions. In another embodiment, a user can delete combinations in a set of possibilities that have been generated before a query of the chemical object database 106 is conducted through the use of a black list, or proviso list. In one arrangement, a proviso list is an instruction to remove values for a moiety variable based on the presence of other moiety variable values. In an alternative embodiment, a set of possibilities can be identified by a user through manual input. For example, a user can draw or otherwise generate one or more moiety variables and define a set of potential values for each user generated moiety variable.

Turning to the illustrated block diagram of FIG. 3, and the flow chart of FIG. 2A, a formula input module 380, configured as code executing in the processor, provides a series of instructions to carry out formula input step 280. This allows a user to obtain or input a generic chemical formula of interest and any associated information about the formula, including potential side chains and backbone structures contemplated by the generic chemical formula. In an arrangement using sequence listings or other non-chemical information, the formula input step 280 uses the formula input module 380 to input sequence listings or other n-gram, syntactic fingerprints or other generic representational data.

Alternatively, the formula input module 380 includes the implementation of an algorithm to automatically input the generic formula or other representational data from the target document. In this arrangement the sequence listings, textual data or chemical descriptors, such as chemical nomenclature, structural formula, or skeletal formula, are converted into a common descriptor format for further processing. For example, the formula input module 380 is configured to use optical character recognition to identify the structural formula of a generic chemical formula provided within the target document and convert those formula features into a common chemical notation or format that can be searched by the chemical database 106. In a further context, or in conjunction with the optical character recognition, image analysis sub-routines are employed to analyze the orientation and positioning of amino acid or nucleotide sequences, side chains and backbones, and convert them into a desired format.

In yet a further arrangement, the processor 102 is further configured by the input module 380 to look up pre-existing descriptors or conversions stored in a conversion table that allow for the conversion of one representational identifier type (e.g. changing a linear chemical descriptor type to a skeletal descriptor) to another. This conversion table can then be updated with pre-approved conversions, or rule-sets, that determine the conversion of one descriptor type to another.

Taking a different approach, a side chain and backbone formula access module 382 configures the processor to allow for manual input of the potential chemical structure formula for some or all of the side chains and backbones. For instance, as shown in FIG. 2B, a user can provide or draw the structural diagrams representing the potential structural forms of the side chains and backbones. In this alternative arrangement, some or all of the structural forms obtained in step 282 are produced manually by the user using a chemical structure drawing program as implemented by a manual generation module 383. For instance, a drawing program such as Accelrys Draw produced by BIOVIA of San Diego, Ca., or an equivalent software module is used to input the chemical formula. Alternatively, the processor 120 is configured by the formula access module 382 to access coded forms of the structural formula for side chains and backbones from a remote chemical formula library or database.

Generating Queries from the Collection of Specific Representational Data

It should be noted that the generic representational data, such as structural formula, broadly describes a range of subject matter, not specific subject matter. Using chemical formulas as an example, the generic chemical formula describes a range of potential chemical structures, as opposed to a specific chemical structure. Thus, in order to search a chemical structure database 106 for overlapping subject matter, the generic chemical structure must be transformed into a computationally useful form conducive for searching a chemical database 106. In a specific embodiment, the computationally useful form is a collection of moiety variables, each moiety variable defining an array of values. The potential values can be one or more chemical identifiers. In an alternative arrangement, the moiety variables define an array having only a single value. The moiety variables are used as a query to search the chemical database. In one arrangement, the query contains, for at least one moiety variable, either the contents of the array of values or a reference to the contents of the array of values. For example, the queries defined according to the query definition step 283 to include a collection of moiety variables representing at least a portion of the side chains and backbone encompassed by the generic formula. Here, each moiety variable will, in turn, define a set (e.g. an array) of potential values for that particular moiety variable.

In one embodiment, a query definition step 283 is implemented by a processor configured by query generation module 384, comprising code executing in the processor, to generate a query, or collection of queries, that represent the generic formula. By way of non-limiting example, and as shown in FIG. 2B, a generic chemical structural formula is input, extracted, or selected by a user for analysis. In the example of FIG. 2B, the structural formula is

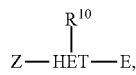

in which $R^{10}$, Z, HET, E and are each placeholder variables representing one of a plurality moieties encompassed by the generic formula (e.g., functional groups representing side chains and backbones). It should be understood that the moieties' variables, such as those represented by the side chain and backbone variables shown in FIG. 2B, are selected or input during step 280 by operation of code executing in the processor utilizing the formula input module 380.

By way of non-limiting example, and in reference to FIG. 2B, according to the generic formula, each of the potential values of side chains Z, E, and $R^{10}$ (each of which can be represented by a varying number of different specific chemical formula components) are combined with the different possibilities representing backbone HET, in order to produce a number of different chemical formula. For ease of description, HET can be any one of pyridyl, pyrimidinyl, pyrazinyl, pyridazinyl or triazinyl. Thus, in one configuration, the five structures are a set represented in the query by a specific moiety variable. In one instance, the specific moiety variable is a reference or pointer to an array populated with each specific value that can be substituted for the moiety variable.

In accordance with the present invention, each of the side chains and backbone are likewise represented by a specific moiety variable that defines the set of potential values for that moiety. For example, Z, E, and $R^{10}$, as well as additional variations (e.g., W and X shown in FIG. 2B), each represent a set of possible values for side chains according to the generic formula.

The query generation module 384 instructs the processor to generate one or more queries in a query language of the chemical database 106. For example, the query generation definition module 384 defines, using the processor, a query string having a number of parameters (each parameter referring to a collection of potential values for a given moiety variable) that when applied to a database, will search the database for specific combinations of the values represented by one or more moiety variables. By generating a collection of queries that describe the generic formula in a computationally useful format, each element of the backbone and side chain arrays becomes available to search the chemical database 106.

The methodology for analyzing a generic formula can be directed so as to focus on specific moiety variables and not others. In this arrangement, the value array for a particular moiety variable can be constrained to as few as a single value. For example, a generic formula can have multiple potential values for a backbone component. However, in order to evaluate a specific subset of the generic formula, the queries can be constructed so as to encompass only one value for the backbone.

One way to generate the moiety variable arrays is to associate the chemical name of a value for each moiety variable with a pre-determined structural formula. In one arrangement this association uses IUPAC naming conventions to extract generic chemical identifiers from the target document and convert the identifiers into a common format.

There are time and computational costs associated with producing large sets of specific chemical moieties. In view of this, a limit step 284 can be implemented using a limit module 385, and used to limit the number of values stored in each moiety variable array and, by extension, the number of queries produced. For example, the query limit module 385 includes instructing the processor to remove, or otherwise blacklist, a specific value or values within an array of values for a given moiety variable.

In the present context, a proviso rule can be incorporated into the query that indicates that specific values described by a given moiety variable should not be searched in connection with a specific value described by a different moiety variable. Proviso rules can be nested such that the presence of a value within the value array of a moiety is dependent, in part, on the values within the value array of one or more other moiety variables. In a further embodiment, the limit module 385 comprises code executing in the processor and instructs the processor using a chemical combination rule set to identify combinations of moiety variable values that will fail to yield search results. There exist a number of different computational chemistry methodologies that can be implemented in the code of the limit module, including but not limited to: scaffold-hopping, and other bioisosteric replacement techniques such as fragment replacement, computer assisted organic synthesis methods, ab initio methods, density functional methods, semi-empirical and empirical methods, molecular mechanics, and molecular dynamics methods that are used to evaluate the success in searching for various combinations of moieties.

In an embodiment which utilizes the limit module so that the query does not include non-viable combinations, computational efficiency is improved by tailoring the search strategy programmatically. Alternatively, the limit module 385 can be configured to instruct the processor to generate a query containing only a partial set of values for one or more moiety variables, or to generate a query that includes only specified moiety variables, and in such an embodiment, a rule base can include a listing of certain variable combinations to be favored over others.

The number of queries, and the size of each array represented by a moiety variable is dependent on the complexity of the generic formula, and the number of the potential variable member sets. As such, in some embodiments, the queries themselves are stored in a local or remote memory storage device, such as a cloud based storage device, that is accessible by the processor 102.

In an alternative arrangement directed to non-chemical subject matter, the claim language of the target document is extrapolated into a series of queries using a query generation module that includes code which executes to configure a processor to implement a natural language extraction and association algorithms to extract data from the text of the target document. In this arrangement, the query generation extraction module utilizes a dictionary of weighted subject matter terms and tokens to extract information from the text of the source documents and convert that information into a computationally useful format. For example, terms commonly used in the collection of patent documents are provided with relevancy weight, such that any extraction will provide discounted values related to the presence of terms commonly found across the collection of source documents. In one embodiment, this relevancy weight is determined by calculating the frequency or uniformity of occurrence of each term in the document or within a collection of documents, or in a larger corpus of text, by assigning weighted values to each term within the document, depending on the frequency of that term or token within the corpus or collection of corpuses selected. For example, common stop words and words common to the subject matter are given a low relevance score. In one embodiment, the relevancy scores are a binary score. In another embodiment the relevancy scores are established relative to a defined relevancy range. In this way a textual fingerprint, such as a numerical or data structure representing the underlying core concepts of the corpus, is generated using the weighted values. In this context, common terms will not be used, or will have reduced relevancy, when generating a numeric representation of the textual elements of a source document that describes the subject matter contained therein. Likewise, terms that have specific technical meanings are given higher weight as they are more likely to describe the specific subject matter of the source document. Thus, collections of terms representing the subject matter of, e.g., each patent document, are generated with each term having an associated value. In a further implementation, the terms are compared to a library of generic features or concepts found within the subject matter, and scored based on the relevance, rarity and/or specificity of the terms found within each source document. These values are then used to convert the terms into a numeric representation of the subject matter of the source documents such that it can be placed within an n-dimensional array of nodes. For example, a syntactic fingerprint representing a document, or of the various potential subject matter contained within the document, is created by generating a multi-bit value or collection of values. These multi-bit values, in one arrangement, correspond to the presence or absence of specific textual elements, tokens, n-grams, or mined sentiment data and are used to identify the scope of the subject matter recited in the target document manifold.

In a further arrangement, the representational data can be directed to biological information, such as nucleotide or amino acid sequences, having generic placeholder values. In this arrangement, the variable portions of the sequences are used to build queries representing some, or all, of the potential sequences that are encompassed by the generic representational data. In a further alternative embodiment, the extraction module implements a biologics extraction algorithm, comprising code executing in the processor, to extract biologic representational data (e.g. DNA, RNA, amino acid sequences) a set of sequences described by the representational data. For example, the queries can comprise a plurality of sequence variables, in which each sequence variable is a reference to a set of nucleic or amino acid sequences.

Alternative Approaches

Alternatively, a query can be defined in a more robust manner, such as when available computational resources permit. In particular, a plurality of moiety variables for a generic chemical formula can have a complete set of known possible values or a defined set of possible values extrapolated into a first array within a memory of a computer. This can be done, for instance, using a query generation module comprising code executing in a processor which has been programmed to implement a robust algorithm to generate a collection of specific chemical identifiers described by the generic identifier.

Searching the Chemical or Representational Identifier Database Using Queries

The queries generated from the generic representational identifier, be it text data, sequence data or generic chemical formula, are compared to a database having entries corresponding to the subject matter and format of the representational identifier.

As an example, the database 106 is searched using queries to uncover similarities between each query generated from a generic chemical formula and the contents of the data. In some configurations the chemical database 106 can be searched directly using the specific chemical moieties in the format they were generated.

In order to access a particular database 106, such as a chemical database, it is necessary to convert the values of each moiety variable into a format that is suitable for searching the database according to the query language utilized by that particular database 106. In one embodiment of the query generation module 384, the processor 120 is further configured to transform the respective, unique combinations of possible values included in the sets of moiety variables, together with any invariant fragment that, together with the moiety variable, defines the chemical identifier, into respective coded representations. In this embodiment, the coded forms are populated to a coded form array that is also associated with a given one of the unique combinations of moiety variables that define the chemical identifier. Thus, the relationship between the chemical identifier values stored in the value arrays and the corresponding coded forms arrays are preserved and stored.

In one embodiment, the chemical identifier values are transformed into an identifier type that is compatible with a specific database query language. This database query language is specific to the database being searched and the coded form represents the conversion of each specific chemical structure into a searchable format that can be utilized by the database operating system or query interface in order to search for the same structure within the entries of the database.

Coded forms for each value in the array represented by a moiety variable are automatically obtained, from the chemical database 106 or an alternative database of side chain and backbone structural formulas. One such coded form is a numerical form suitable for binary key manipulation. In one particular instance, the processor 102 is configured to convert the collection of possible formulas represented by the generic formula by converting each generated formula into a computationally usable chemical formula form (i.e. coded forms produced by a MDL 960-bit SS-keyset numerical conversion algorithm).

The query is applied to the chemical database 106 according to step 285. In a specific arrangement, a database search module 386 instructs the processor to compare the unique combinations of the possible values stored in the arrays of one or more moiety variables, including any invariant fragment, so that the comparison is of the uniquely defined chemical identifiers that correspond to the generic chemical formula to the entries in the chemical structure database 106 in order to identify a complete or partial overlap of subject matter.

Likewise, in arrangements not directed to chemical subject matter, the queries are searched against a database of subject matter terms that have references, links or associations to the documents of the source document database. For example, BLAST and other sequence similarity tools are used to compare the query results obtained from a generic nucleotide sequence with nucleotide sequences stored in a database 106.

Results from the Database Query

The results of the database search indicate the presence of specific instances of representational data, formulas or other information within the source documents that are encompassed by the generic representational data extracted and extrapolated from the target document.

Using the results module 387, which in at least one embodiment can comprise code executing in the processor, the processor implements step 286 and adds the database entries that match the query to a data collection. For example, when a matching database record is found, a reference or data object corresponding to the matching structural formula and any linked data is stored in the memory of the processor or other computer as an entry in a collection of positive matches.

After each or all of the queries are searched against the database, the collection is output using output module 388 to a visual display (e.g. as a list or map, as described below), a storage device, or to other modules for further use. In a particular embodiment, the results module 387 includes a submodule for conditioning the results, as provided in step 287. For example, if the results are obtained from multiple different databases, it is necessary to condition the results so that all the entries are represented in the same data type.

In one arrangement, the visual output of the collection of positive matches identifies those source documents that describe specific representational identifiers encompassed by the generic representational identifier. In a further arrangement, the collection of positive matches also includes information indicating the specific values of each moiety variable described in the query that resulted in such positive matches.

In a further arrangement, the positive matches include the links to the source documents containing specific formula that are encompassed by (i.e., included within the scope of) the generic formula found within the target document. For example, a source document can be a published or unpublished patent document that references a plurality of chemical identifiers.

The collection of positive matches of database entries encompassed by the query can be used or stored for further analysis. Alternatively, the collection is passed as input, according to step 287, to either of steps 230 and 240 of the mapping system described herein, as may be appropriate, and the method of FIG. 2 can proceed to the visualization step 260. If the collection contains coded forms of the query matches, the collection is sent as input to the plotting module 340. Alternatively, if the collection contains non-coded forms, or if the forms are in an incompatible format with the mapping system, the collection is output to the conversion module 330 and then passed to the plotting module 340 as in steps 230 and 240.

In accordance with one embodiment of the invention, a subject matter similarity analysis, as shown in steps 280-287, is used to identify source documents of interest, i.e., those source documents having overlapping subject matter with the target document. In this embodiment, a generic structural formula is used to query a chemical structure database in order to find source documents that describe the same subject matter as the generic structural formula.

However, in a further implementation of the present invention, the search queries are conditioned to identify representational identifiers that have a threshold of similarity with at least one specific representational identifier encompassed by the generic representational identifier. In this configuration, if the search of the database yields no results, indicating that none of entries in the chemical database 106, and/or the source documents database have overlapping subject matter with the generic formula, then the search queries can be modified in accordance with this implementation to be broader, such as by removing side chains until the search of the database yields results. For example, the processor 102 can be configured by code to implement an iterative search algorithm that removes or alters side chains or backbones of a generic chemical formula extracted from a target document.

In the event that the search results include only partial matches to at least one of the generated queries, the search results can be plotted, mapped and analyzed for the degree of similarity between the formulas.

Determinations Based on the Results

The results of the query generation and visualization system are used to identify overlap between a generic formula in a target document and chemical identifiers found in a source database or in source documents linked to a chemical database. In one configuration of the system, the source documents are patent documents disclosing a plurality of chemical identifiers. In this arrangement, when the generic formula is determined to encompass subject matter found in multiple patent documents due to matching, as described above, the system is configured to provide a visual indicator corresponding to the source documents containing the highest subject matter overlap with the generic formula. That collection of source documents can be identified by sorting to group the highest scoring overlap results together.

For example, in a circumstance in which multiple source documents contain overlapping subject matter with the generic formula, the system is configured to identify the closest source document(s) by grouping the positive results by bibliographic data linked to each entry in the chemical database 106, and the grouped results are output to a display (and optionally to a hardware storage device).

The system has applicability to identifying overlapping subject matter in source documents. Additionally, the system can be used to identify the overlap of subject matter between a plurality of generic formulas. In this configuration, each generic formula is used to generate a collection of queries encompassed by the generic formula. According to this arrangement, the collection of queries, so obtained, can be used in a query in lieu of source documents or a source document database. As such, each collection can be compared to all of the other collections, and any matches will represent overlapping subject matter between or across different generic formula.

In an arrangement analyzing non-chemical subject matter, the results can be used to identify subject matter similarity between patent documents or between the claims of a target document and a textual description of a potentially infringing product or process.

One use of the results, whether the results relate to chemical identifiers or not, is to identify the duplication of subject matter across a commonly owned patent portfolio. Based on the degree of overlapping subject matter, the system is further configured to identify a pending patent document that can be abandoned since the subject matter of concern is already secured by a different commonly owned application. Alternately, the system can be used by patent officials to examine applications, especially complex chemical compound disclosures to identify prior art and possibly double patenting concerns.

In another implementation, the results are used to manipulate the potential values for at least one of the plurality of moiety variables. This change in the scope of the potential values associated with one or more moiety variables is useful in generating an updated generic formula that only encompasses novel entities (e.g. ones not matched in the database) or anticipated entities (e.g. ones encompassed by the database). In accordance with this further aspect of the invention, the elements in a value array associated with a moiety variable can be divided into one or more divisions based on the presence of the members of the division in the positive match search results. In one implementation, values for a moiety variable that are present in one or more one positive matches returned by the database are identified. These common values are used to restrict the potential values the moiety variable to only those values that are present in the members of the given division.

In an alternative configuration, each moiety variable value found in each of the members of the given division is identified and used to build Markush groups for each of the moiety variables. For example, the unique value of every backbone and side chain present in the members of a given division is assigned to a corresponding Markush group. In this way, the generic formula using these generated Markush groups will only describe the members of the selected division. As a result, the scope of the generic formula can be modified or reduced to only encompass a subset of the original chemical formula based on user preference. The reduced scope generic formula can be output to a memory or display for further use or storage.

Sequences are then converted into a numeric representation of the representational data such that it occupies a space within an n-dimensional manifold. In another arrangement the data extracted is data relating to antibodies and antigen binding fragments thereof including antibodies from various animals, humanized, chimeric, polyclonal, monoclonal, bi-specific, multi-specific, single chain antibodies, Fab fragments, $F(ab')_2$ fragments, disulfide-linked Fvs, fragments containing a VL or VH domain or a complementary determining region (CDR), wherein the antibody or antibody fragment immunospecifically binds to a peptide, polypeptide or protein that is described in a collection of source documents.

In order to fully implement the mapping system as described herein, and more fully described in the aforementioned U.S. provisional application No. 62/023,006, the following features, systems and methods are provided.

With reference to FIGS. 2 and 3, the positive matches, indicating overlapping subject matter between the generic formula and the source database or subject documents, are mapped to a virtual n-dimensional node array, as described in more detail below, in order to identify the degree of similarity between all of the positive matches identified. As explained further below, each chemical identifier extrapolated from the generic representational identifier, or returned as a positive match from the search the database, can be placed within a virtual node array such that the similarity between positive matches, or any of the extrapolated forms can be visualized.

Temporal Visualizations

Data used to generate the virtual node array can be visualized using a visualization module 360. The processor is configured using code that implements the visualization module 360 to display the data entered into the virtual node array as a function of time, common assignee, database or origin or other bibliographic data that is associated with the data. For example, the visualization module can configure the processor to display a time series of plots, where each of the elements of the series relates to a chemical identifier described in a document owned by a common assignee at a given period in time. Through the use of visualized virtual node arrays, the system and method enables the discovery of relationships between extrapolated data and the source documents that are not perceptible from the mass of raw data.

For instance, in connection with computer-assisted drug discovery, it would be of interest to track a company's patent filings over time. Existing systems might be configured to include temporal data in the information that is being displayed, but systems are not adapted to provide an animation. Rather, tracking more than one assignee, company or entity over time over time can clutter the display and become unwieldy. One solution is to add additional markers or identifiers to both track companies and time periods, but such solutions only diminish the usefulness of visualizations.

The system and method provided, improves on these systems by providing a visualization that implements a collection of identifiers to both group data (e.g. chemical identifiers) by source, but also to identify temporal and other bibliographic data. The visualization module 360 configures the processor to generate temporal snap-shots of the generated visualization such that discrete time periods can be viewed as sequential images or as an animated progression, using code to manage the time-window of data presentation. The animated progression can, in one arrangement, indicate the publication of source documents describing positive matches over time. In a particular aspect, the visualization module includes generating an animation that displays the publication of the source documents, for specific assignees or institutions over time, by assigning both indicators to temporal ranges and to assignees.

In a further aspect, financial data associated with each assignee can be linked to the visualization and displayed so that the financial status of an assignee at a given point in time is displayed along with publication rate of source documents.

The extraction module 320 can be arranged to include sub-modules that transform the text and the bibliographic information into a data object or record. In particular, the extraction module or its sub-modules can include code that configures the data object to populate fields included in the data object's definition with data elements unique to the source document, such as the patent or application number, the name of the inventors, assignment status, date of filing and other bibliographic data. Alternatively, the data object can comprise a database entry, a record, a linked list, and so on, all of which can enable the operations described below in regard to data objects.

Optionally, the extraction module 320 can further comprise code that configures the processor to In another aspect in which the system and method are utilized to generate new or predicted generic representational identifiers, the visualization module can be used to generate visualizations of the scope of the representational identifiers represented by each newly-generated, generic representational identifier. In this case, the visualization can demonstrate the change in the scope, e.g., how many source documents are returned as a search result of different generic representational identifiers generated.

The following describes, in detail, the process of converting the data generated in the extrapolation and query processes into suitable formats for use in the visualizations and animation concepts described.

Conditioning the Source and Target Formulas

The processor 102 is configured to implement extraction a secondary filtering step 222. For instance, the second filtering can comprise code that eliminates data objects that concern salts, crystalline or amorphous forms and other duplicative or similar entries of a particular chemical entity. Upon completion of the extraction and filtering steps 220-230, in order to condition the chemical formulas that represent positive matches for use in further process steps. 222, the process stores the filtered results in the chemical entity data object database 106 or elsewhere, as noted above.

In order to utilize the data stored in the chemical entity data object database 106, the processor operates on the text in the source documents to convert the text that the extraction module identifies as relating to a given chemical identifier into a coded form suitable for further processing. In one example, the coded form is a numeric value (e.g., a keyset) representing the structural, physical and/or binding properties of a given chemical compound.

In one embodiment, a conversion module 330, which can comprise code executing in the processor, configures the processor 102 to convert each chemical identifier into a coded form according to a conversion step 230.

In yet a further embodiment, the conversion module utilizes image recognition sub-modules to obtain chemical names or formulae from a given structural formula, such as a skeletal formula. For example, the conversion module 330 configures the processor to compare a structural formula under investigation to a plurality of known structural formulas, each associated with a specific chemical formula or chemical name, and to identify the chemical formula based on a match within a prescribed criterion(ia) between the two.

In an alternative configuration, the conversion module 330 comprises code executing to configure the processor 102 to compare peptides, polypeptides, nucleotide sequences, or any fragments, domains, or regions relating thereto.

In yet a further embodiment, the conversion module utilizes image recognition sub-modules to obtain chemical names or formulae from a given structural formula, such as a skeletal formula. For example, the conversion module 330 configures the processor to compare a structural formula under investigation to a plurality of known structural formulas; each associated with a specific chemical formula or chemical name and identify the chemical formula based on a match within a prescribed criterion(ia) between the two.

Converting all Representational Identifiers to Computationally Useful Forms

In a further embodiment, the conversion module 330 can configure the processor to convert the chemical identifier of each positive match of a chemical identifier (as used here in the positive matches are referred to as chemical entity data object (CEDO) into coded forms and store the converted forms in a memory or other storage location while preserving the association between the CEDO and the coded form. In one embodiment, the conversion step 230 includes the embodiment of a MDL 960-bit SS-keyset numerical conversion algorithm, produced by MDL Information Systems, in order to convert the identifier into a numerical representation. Alternatively, other keysets such as, for example, those based on affinity-fingerprint algorithms or feature-tree algorithms, or the 881 bit structural keys used by PubChem, or 1- and 2-dimensional molecular descriptors can be implemented by the processor 102 in order to obtain coded forms of chemical identifiers.

Once the numerical forms, or other coded form conducive for similarity determinations, have been obtained by implementing step 230, or have been obtained as an output from the subject matter similarity module according to steps 280-287, the coded forms are evaluated for their similarity to one another. In one embodiment of the system and method, a plotting module 340 is used to configure the processor 102 to conduct a similarity analysis on the plurality of numerical forms obtained and stored in the previous steps. In one embodiment, the plotting module 340 comprises code that configures the processor to plot each of the CEDOs, as noted at step 240. The plotting module 340 includes code that executes so as to configure the processor 102 to plot the numerical forms to an n-dimensional, preferably low-dimensional, manifold using a dimensionality reduction algorithm, such as a self-organizing map or other type of neural network or machine learning algorithm or system.

As used herein, neural networks are machine learning systems used to derive rule bases for evaluating unclassified data using pre-classified or "training" datasets. These rule bases are instructions that configure a data analysis agent, such as a processor, to classify new data passed to the system. Furthermore, the rule base is configurable such that the rule base itself is updatable, extensible or modifiable in response to new unclassified data. In the embodiment provided, the CEDOs are used both as the training data and the unclassified data.

Analysis of Biologics

As shown in FIG. 2B, a biological target is selected for analysis and evaluation. In the present context, the biological target of interest is a disease or disorder. For instance, the biological target is selected from any type of cancer e.g., leukemia and lymphoma, carcinoma, sarcoma, blastoma, or germ cell tumor. In another embodiment, the biological target is an autoimmune disorder. In a further arrangement, the biological target is a disorder of the skin, heart, lung, liver, bone, brain, stomach, colon, breast, prostate, bladder, kidney, pancreas, ovary, and/or uterus, lymphatic or nervous systems.

In an alternative configuration, the biological target is an antigen, or a specific class thereof, e.g. Tumor Necrosis Factor (TNF). For example, the search step 210 yields all of the documents within the document database that describe TNF inhibitors.

In a more detailed example using TNF, the search results contain references to biological identifiers or entities, such as antibodies from various animals, humanized, chimeric, polyclonal, monoclonal, bi-specific, multi-specific, single chain antibodies, Fab fragments, F(ab')2 fragments, disulfide-linked Fvs, fragments containing a VL or VH domain or a complementary determining region (CDR), wherein the antibody or antibody fragment immunospecifically binds to a peptide, polypeptide or protein or sequences describing the same.

The biological identifiers described in each search result are extracted to the database according to step 210. In one particular arrangement, the extraction of step 220 is accomplished by extracting the light and heavy chain amino acid sequences from the sequence listings associated with the documents. In a further arrangement, the biological entities or identifiers found in the search results are matched to existing entries in a database that contains a plurality of biologic identifiers associated with the same biologic entity.

According to step 220, the extracted biologic identifiers found in the results are stored in a database as individual biologic data object (BDO) entries. These entries include the biological identifier (e.g. a sequence of amino acids) and bibliographic data indicating the source document. Depending on the format of the data stored in the database, the biological identifiers can be directly mapped to an n-dimensional space, or first converted into a coded or numerical form as in step 230.

As an example, the conversion step 230 includes a sparse binary conversion algorithm to convert the biologic identifier stored in a BDO into a numerical representation. Alternatively, affinity-fingerprint algorithms or feature-tree algorithms, or other algorithms can be implemented by the processor 102 in order to obtain coded forms of the biologics identifier. In another arrangement, the sequences are converted using a multi-bit keyset into a multidimensional identifier. For instance, each potential value for a position in a sequence is given a multi-bit value and the multi-bit values taken collectively, represent the sequence. In an alternative arrangement, the BDOs are converted using a substitution matrix employing PAM, PET91, BLOSUM algorithms to generate a specific numerical identifier for each amino acid in a sequence. The generated numerical sequences are compared to one another to determine similarity of the sequences.

Regardless of the conversion metric applied, the converted numerical forms are associated with the source biological identifier and are plotted to n-dimensional space according to steps 240-250, as discussed previously in connection with FIG. 2A. The distances between and among the plotted numerical forms provides a basis for a processor, executing code, to make a comparison and resulting similarity determination among the sequences, such as by calculating the smallest distance within the virtual n-dimensional space.

Analysis of Hybrid Structures

In a particular arrangement of the present invention, the biological target searched is a hybrid structure. A hybrid structure can be a combined protein and small molecule complex engineered to exhibit improved pharmacokinetic characteristics, e.g. improved half-life of the small molecule. According to this configuration, the biological target is the search criteria for hybrid complexes, or for the individual biologic and chemical components of the complex. As an example, a hybrid structure utilizing a biological macromolecule (protein) coupled to a sodium channel inhibitor conferring improved half-life is searched using a strategy that identifies sequences for long half-life macromolecules and sodium channel inhibitors. In one implementation, identification of such sequences can be performed using a processor executing code that extracts from a corpus of source documents any references to a sequence described in a given document that satisfies the target criteria (e.g., certain pharmacokinetic properties). The similarity of biological identifiers (e.g. amino acid sequences) is assessed, generally as described above, using a plot of a virtual landscape, constructed by a suitably programmed processor.

Next, the similarities between the sodium channel inhibitors are assessed. In one arrangement, the biologic and chemical components of the hybrid structure are weighted based on relevant factors. As one example, a relevant factor can be whether the search for the hybrid target yielded more sequences than sodium channel inhibitors. As another example, a relevant factor can be the binding affinity of either the biologic or the chemical component of the hybrid structure. Based on the weighting approach being utilized, the sequences are plotted, the sodium channel inhibitors are plotted, or a combination of the two is plotted to a single map. Alternatively, the biologic identifiers are plotted to a first n-dimensional array and the chemical identifiers are plotted to a second n-dimensional array. In this configuration, an indication of the relationship between the biological identifier component of the hybrid structure mapped to the first n-dimensional map and the chemical identifier component of the hybrid structure mapped to the second n-dimensional map array can be maintained.

Once the numerical forms or other coded form conducive for similarity determinations have been obtained by implementing step 230, the coded forms are evaluated for their similarity to one another. In one embodiment of the system and method, a plotting module 340 is used to configure the processor 102 to conduct a similarity analysis on the plurality of numerical forms obtained and stored in the previous steps, as described herein. In one embodiment, the plotting module 340 comprises code that configures the processor to plot each of the CEDOs, as noted at step 240. The plotting module 340 can include code that executes so as to configure the processor 102 to plot the numerical forms to an n-dimensional, preferably low-dimensional space, such as a 2-dimensional or 3-dimensional space. That code can implement a dimensionality reduction algorithm, such as a self-organizing map algorithm or other form of neural network/machine learning algorithm.

Discussion of Chemical Entity Data Object Examples

The following discussion uses CEDOs as an example of the functioning of the system and method provided. However, it will be appreciated by those possessing the requisite level of skill in the art that BDOs or TDOs can be substituted for CEDOs when used in conjunction with corresponding databases 106, according to the following steps.

Plotting the Converted Formulas

In the illustrated embodiment, the plotting module 340 configures the processor 102 to generate an n-dimensional space as the landscape and seed it with placeholder values, as noted at step 242. The placeholder values in this example are selected to cover the range of potential numerical values for the converted coded (e.g., numerical) forms of the CEDOs. In a particular embodiment, the plotting module 340 includes code to further configure the processor to insert each CEDO at a location in the n-dimensional space, such as according to step 250. In the illustrated example, the particular location for the insertion operation is a function of the degree of similarity that the coded form shares with the placeholder data or to other coded forms previously placed in the n-dimensional space. Here, the coded forms are used to plot the CEDOs to a given coordinate location in the n-dimensional space according to the similarity of the coded forms of each of the CEDOs to one another and to the placeholder values. It should be understood, however, that one embodiment of the invention utilizes the plot coordinates to compute the degree of similarity without actually plotting the CEDOs to an output device.

Discussion of Plotting and Placement Module Example

Figure 4:
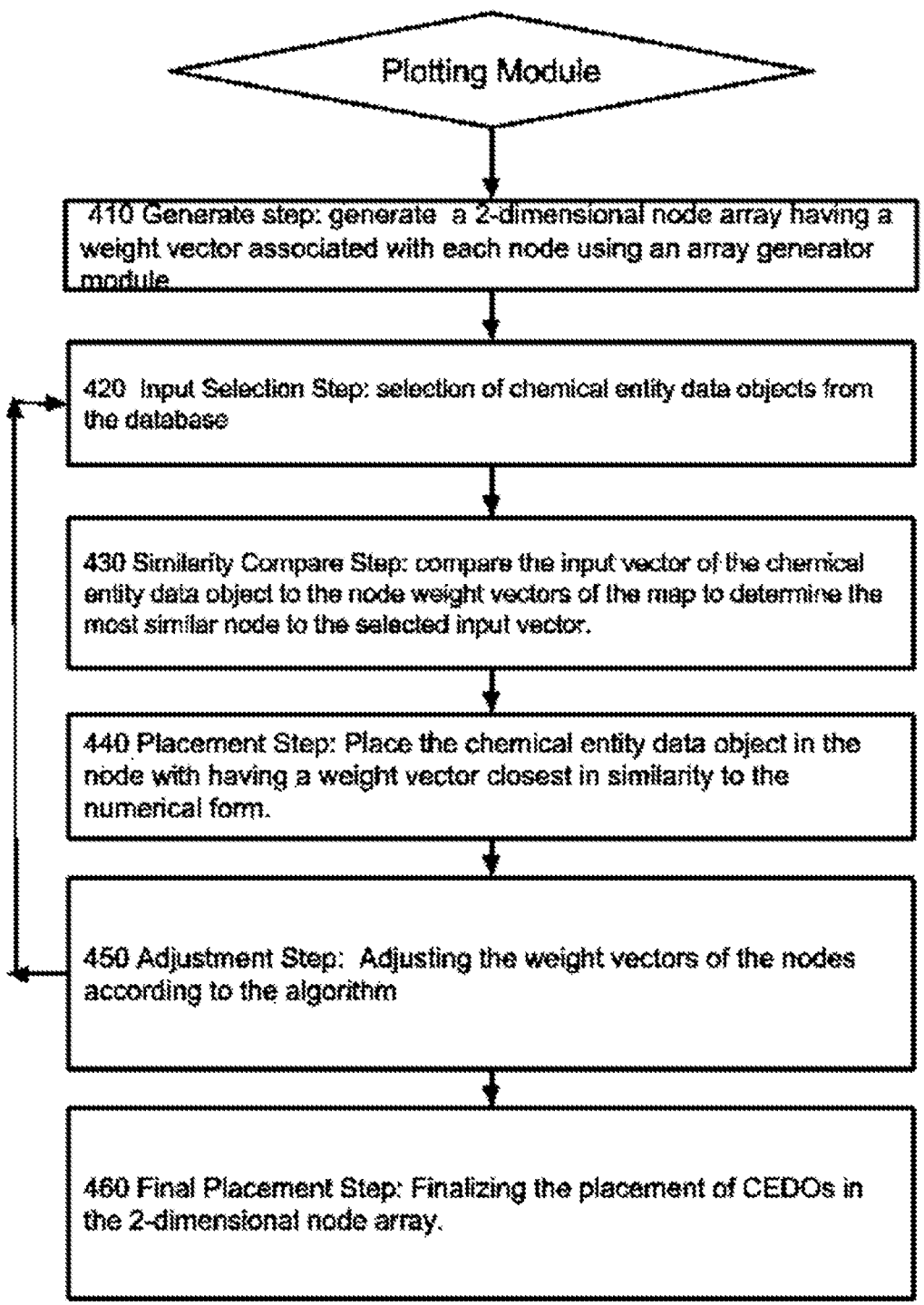
FIG. 4 is a diagram of the operation of the plotting module according to certain embodiments of the system described.

FIG. 4 provides a detailed view of the subsidiary steps that can be performed as part of the operation of the plotting module 340 when the dimensionality reduction algorithm comprises a self-organizing map. The steps implemented therein as 410-450 are provided for illustrative purposes and are not restrictive, and may not be representative of the steps that would be utilized in order to implement a different algorithm but the variation to implement different algorithms would be understood by persons of skill in the art.

In this particular embodiment, the plotting module 340 configures the processor to execute code in order to compute a degree of similarity (determined by calculating the Euclidean distance between the coded form and a weighted vector placeholder value) and placement of CEDOs according to the following self-organizing mapping algorithm:

$$Wv(s+1)=Wv(s)+\Theta(u, v, s)\alpha(s)(D(t)-Wv(s))$$
$$\text{while } s \leq \lambda, \quad \quad \text{EQ(1)}$$

In the example equation above, the algorithm is implemented as an iterative calculation. For example, the processor 102 is configured by code to iterate over the collection of CEDOs according to the above equation so long as S (the current iteration) is less than a user or computer provided iteration limit (e.g., $\lambda$).

In the above equation, Wv represents the current weight vector of node v. Furthermore, v represents the index of the node in the map, while u represents the index of the best matching unit (BMU) in the map. $\Theta(u, v, s)$ represents a restraint function value derived from the distance between the BMU and the input vector. Typically, this restraint value is called the neighborhood function and is used to calculate how the weight vector of a node is modified during the course of each iteration. $\alpha(s)$ represents a learning restraint due to iteration progress. Collectively, the CEDOs operate as data vectors and as such the entire CEDO collection is regarded as input data set D and the particular CEDO under analysis operates as D(t), where t operates as the index value of the target input.

In the process steps of FIG. 2, the processor is configured by the plotting module or its respective sub-modules, to generate a landscape in the form of a two dimensional virtual node array, as indicated at step 410 of FIG. 4. The node generation step can operate to produce a two-dimensional node. However, the sub-modules are configurable to generate multi-dimensional nodes, such as, for example, a three-dimensional node. In this particular embodiment, the nodes of the array are pre-seeded with weight vectors. The weight vectors, in one embodiment, are assigned random variables within the range of possible values based on the data set.

The plotting module 340 can further comprise code that configures the processor 102 to implement a CEDO selection process, as indicated at step 420. In this step, the processor selects a CEDO from the chemical object database and assigns the selected CEDO to a given coordinate location within the virtual node array. In one example, the CEDO is placed in the virtual node array according to the numerical form of the chemical identifier unique to that CEDO, in a virtual location defined by the self-organizing map, for example.

Optionally, the plotting module 340 further configures the processor to implement a similarity/identity analysis using algorithm EQ1 (above), as indicated at step 430. Thus, in one embodiment, the processor is configured to compare the input vector for a given CEDO (coded form) and the weight vectors. For example, the processor is configured to calculate the distance between the input vector and the weight vector, as indicated at step 430, where the distance between the input vector of a CEDO and the weight vector of the map's node is related to the degree of similarity between the weight vector and the input vector values. In a particular embodiment, the distance formula is a Euclidean distance formula. In a further embodiment, the processor 102 determines which node in the map provided by the virtual node array produces the smallest distance between a given CEDO and the weight vector of any node (i.e. a "best matching unit," or BMU).

The plotting module 340 further includes code executing within the processor in order to implement a placement step 440. The processor 102 is configured to place selected CEDOs, according to the input vector, into a virtual node having a weighted vector with the closest similarity. Once an initial placement occurs, the placement step can subsequently adjust the weight vector value of each node in the array depending on the current placement, as indicated at step 450. In one embodiment, the processor configured to make the adjustment of step 450 using code executing therein to update the placement of the CEDO in the map nodes that are in the neighborhood of the BMU, including the placement of the BMU itself.

In a further embodiment, this is accomplished by adjusting the node weights stored in the processor memory relative to the recently added CEDO. In this way the CEDOs placement in a particular node of the virtual array is revaluated based on the BMU value and each input vector value.

The "neighborhood" as described herein, defines a set of neighboring nodes characterized by certain parameters such as distance from a BMU (best matching unit) and a shape of the neighborhood function. In a further embodiment, "neighborhood" references the maximum distance that an input vector can be moved while still remaining within a particular node.

Once a CEDO has been placed according to the adjustment step 450, the process iterates from step 420 to 450 with each new CEDO. This iterative process is commonly referred to as "training" or "seeding" the node map.

In some embodiments this map seeding subsequence is iterated several times for each CEDO in order to properly adjust the node weights for all of the CEDOS that have been included into the map so far.

Once all of the CEDOs have been seeded into the map, a final placement step 460 is implemented by a processor 102 configured to execute a final placement sub-module of the plotting module 340. In this embodiment, each of the CEDOs is finally placed at a given coordinate location within the virtual node array according to the input vectors and the weight vector of the nodes.

Placement includes the intermediate step of assigning the coordinate locations according to the input vectors and the weight vectors of the nodes and the step of plotting the CEDO at the given coordinate location on an output device (e.g., display, printed report or data file).

The self-organizing mapping functions that have been detailed at steps 410-450 comprise one non-limiting embodiment of a dimensionality reduction algorithm. Other dimensionality reduction algorithms using neural networks or other analytic techniques are also useful in converting high dimensional datasets to low dimensional datasets. Examples of such techniques, such as feature extraction algorithms, and feature section algorithms are useful for organizing and visualizing the data according to the present system and methods.

In a further embodiment, a combined latent class and trait model, as described in Ata Koban, A combined Latent Class and Trait Model for the Analysis and Visualization of Discrete Data, 23 IEEE Trans. Pattern Anal. Mach. Intell. 859 (2001), incorporated by reference herein as if fully set forth in its entirety herein, is used to analyze and evaluate the CEDO data obtained from the source document. In this embodiment, the latent class distribution can be represented using the Koban equation as taught in the above journal article, as:

$$p(c) = \sum_{k=1}^{K} \delta(c - c_k) P(c = c_k) \qquad \text{EQ 2}$$

Where $$\sum_{k=1}^{K} P(c = c_k) = 1$$

In the provided equation, the L-dimension variables c can be considered as a uniform sampling from the corners of a K-dimensional hypercube, with $\delta$ being a distribution function. Furthermore, the latent dimension is K and one value of c is denoted by ck.

This latent class model can be combined with a latent trait model represented by a 2-dimensional grid of points X, where X=M×K and M=2 (e.g., 2-dimensional) and this model is mapped by a set of L nonlinear and linear basis vectors $\Phi 1$ such that $$C = C = \Phi(X) \qquad \text{EQ2}$$

Where C is an L×K dimensional matrix.

The CEDOs are evaluated according to the above equations and mapped to a 2-dimensional grid based on the relationship of each individual CEDO to one another.

Other placement algorithms, including without limitation, smallest distance metric algorithms, can likewise be utilized by the systems and methods described herein.

Discussion of Visualization Module Example

Once the data objects that represent the unique numerical forms, or other coded form of the chemical identifiers have been plotted to the n-dimensional virtual space, the results of the plotting module 340 can be presented to a user through data visualization. In one embodiment, a visualization module 360, operating as code executing in the processor 102, configures the processor to generate visualizations of the data plotted according to the plotting module 340 on a display device or printer. In another embodiment, the plot coordinates are stored without use of a visualization engine.

For example, the processor 102 can be configured to implement step 260 in order to provide a user with a visual display of the CEDOs based on the similarity of the input vectors. Depending on user input and selection concerning what is to be depicted within the virtual node array, the visualization presented to the user can provide markers which represent each CEDO stored in the chemical entity data object database 106 (or elsewhere) and the corresponding placement of that CEDO within the virtual n-dimensional space. Visualization modules suitable for use in embodiments of the invention can include a variety of commercially available visualization systems 108. One such example is the Spotfire product of Tibco Inc., Palo Alto, Ca. Alternatively, the visualization module can be constructed as described herein for NCE visualization purposes.

FIG. 5A depicts one non-limiting type of visualization of a collection of CEDOs for a given biological target. Alternatively, the collection of CEDOs can comprise the positive matches obtained from step 287. The data is arranged as a 2-dimensional array, where each individual CEDO has been plotted based on the similarity of the CEDOs to one another and to the weighted value of the node. In the illustrated example, the visualization module 360 provides a 2-dimensional grid on a display 400 or other output of the computer. However, in alternative embodiments, the visualization module 360 may display higher dimension visualizations. What can be appreciated, more generally, is that the placement of a given CEDO within the virtual node array is a function of the training that the array undergoes as each CEDO is added. As such, the similarity comparisons of chemical features, as described below, is a function of the virtual distances which owe their values to the placement and repositioning of CEDOs during training as the node-array is populated.

In one non-limiting embodiment, the visualization data presented to the user includes bibliographic data relating to the source document and the linked chemical identifier. In the illustrated data visualization (FIG. 5A), each marker 402 represents a different chemical entity. Likewise, a color of each marker 402 represents a different assignee for the originating source patent document. The shape of each marker, such as the triangle, corresponds to a single, common source document for each assignee. More generally, the markers are specified by rules stored in a memory 110 which are used by the visualization module 360 to influence output by the system to a display screen, printer or other such device.

In another implementation, the visualization data presented to the user includes additional content information obtained from external content sources. For example, the visualization module includes an external content sub-module or associated module that configures the processor to obtain external content relating to the CEDO, or the patent document that is the source of a particular CEDO. For example, the external content sub-module is configured by code executing in the processor to identify external content relating to the CEDO or its source document. Such sources can include legal judgment databases, social media networks, regulatory (e.g. FDA, SEC) databases, scientific and technical journals, sales and marketing databases, and business development resources, license agreement records. These external content sources provide primary or secondary identifiers that can be applied to the CEDO. In one instance, a CEDO is marked with a particular color representing ownership status, but is also marked with a particular symbol indicating that it has been licensed to a third party. In this way multi-dimensional information is conveyed in the visualization.

As shown FIG. 5A, markers 402 are clustered to particular coordinate space locations within the provided 2-dimensional space. In the illustrated embodiment, each cluster of markers 405 represents a collection of markers having a similar chemical identifier, such as can be determined by a self-organizing mapping algorithm as discussed above. In the event that no chemical identifiers have a similarity within prescribed criteria to a given coordinate location, the node is rendered in the visualization as an empty node or gap 406.

FIG. 5A provides a complete view of all the CEDOs obtained as a result of the inquiry in accordance with one embodiment of the invention. In various alternative embodiments, it is useful to organize the data according to the input vector (such as the numerical value representation of the chemical identifier), yet also display the data according to other features of the CEDO.

Figure 5B:
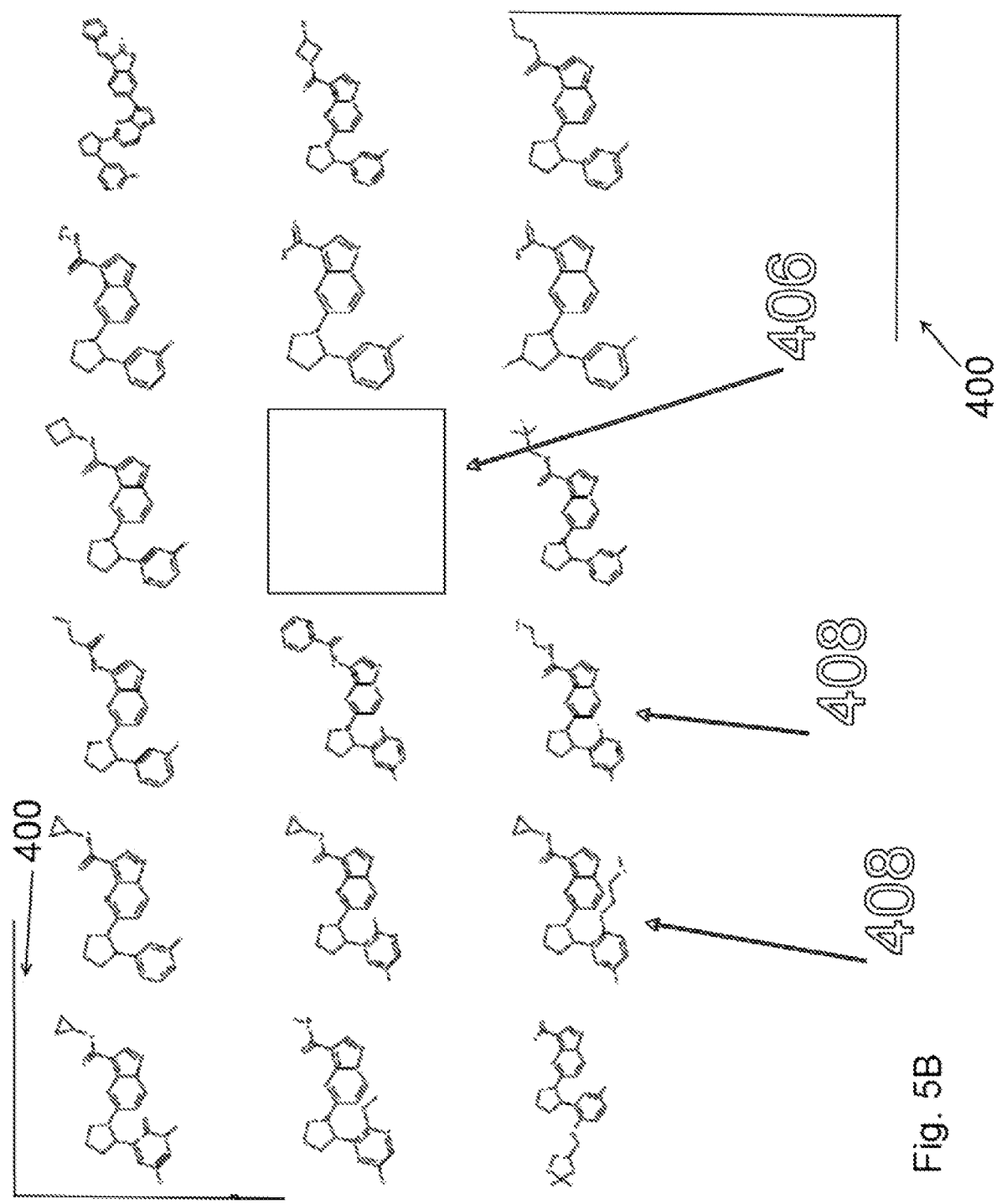
Figure 5C:
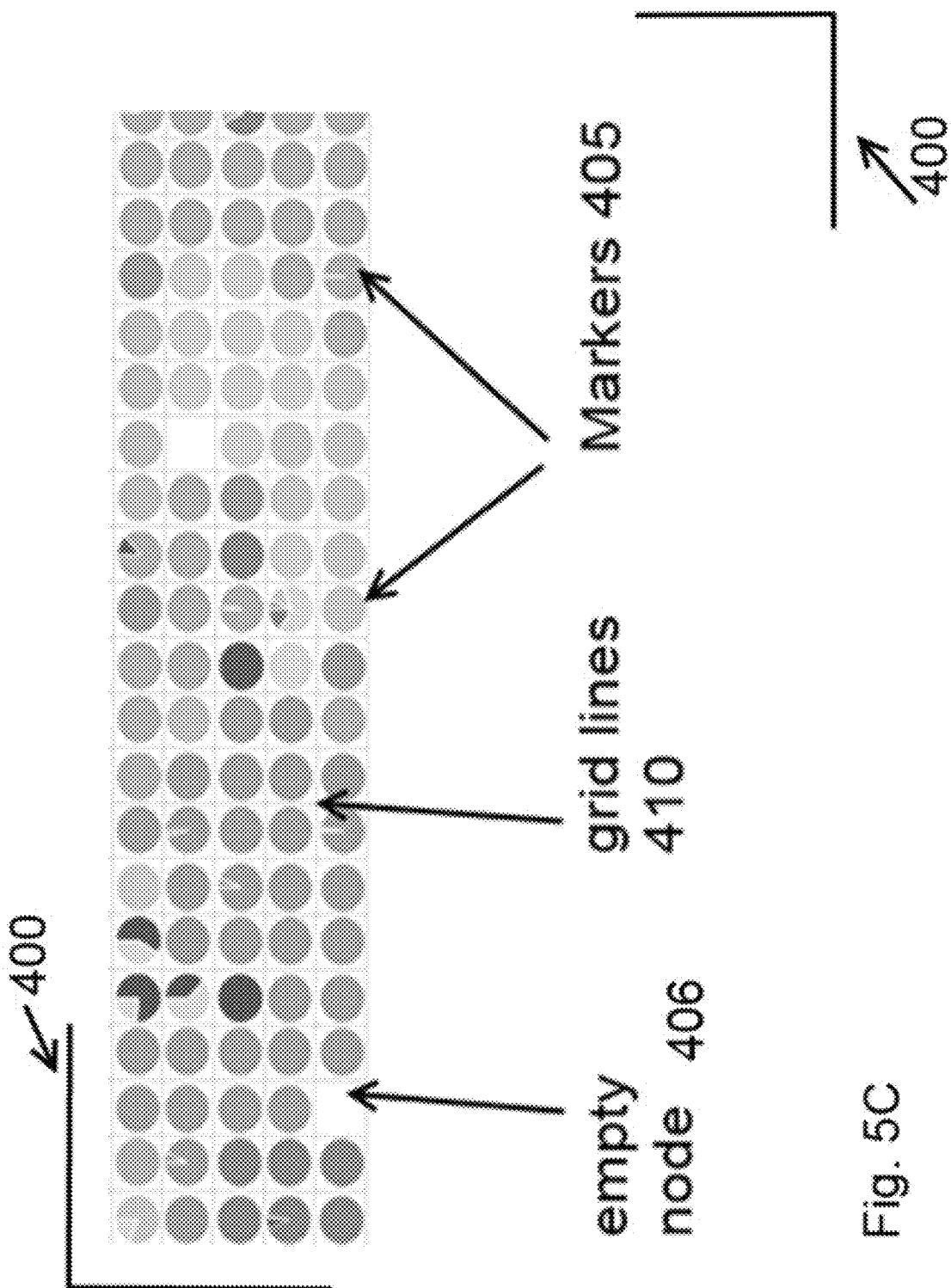
Figure 5D:
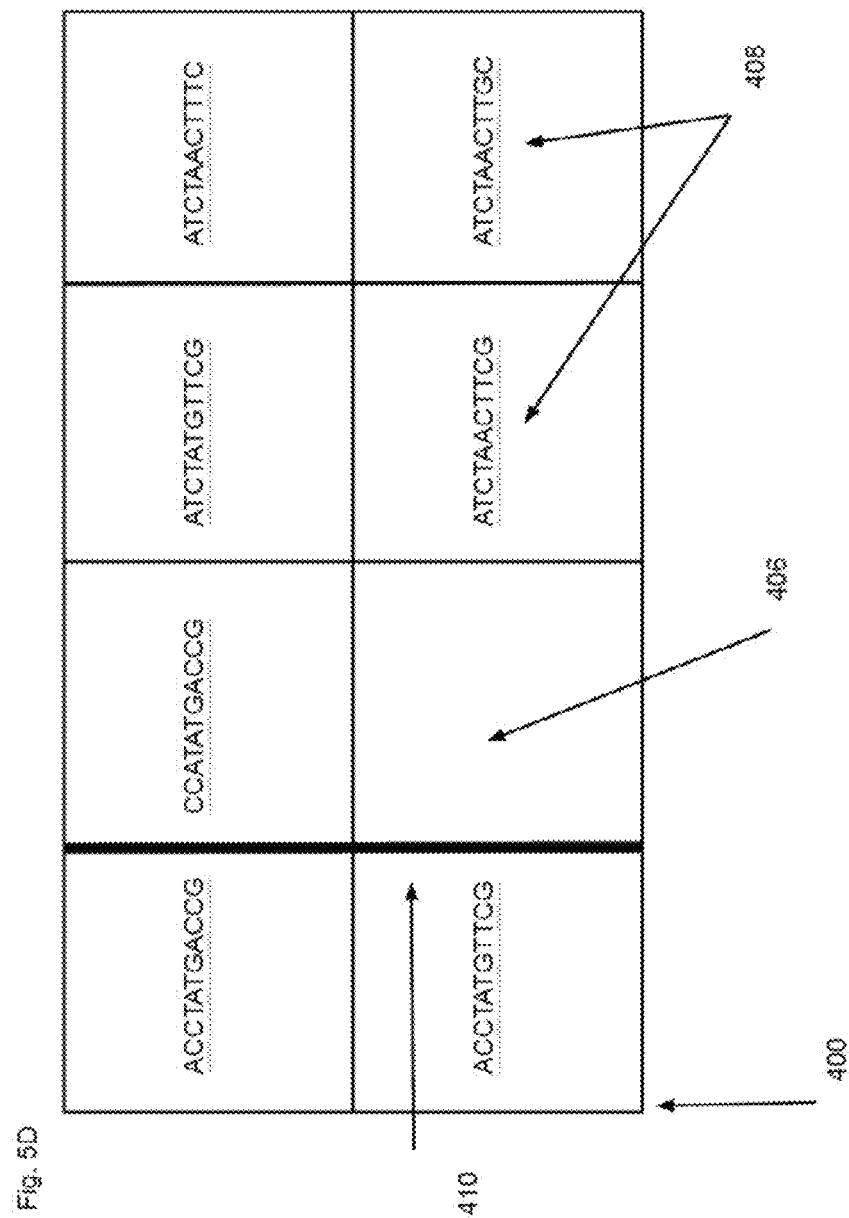

As shown in FIGS. 5B and 5D the visualization module operates to output—to the display 400 or other output device—the original biologic or chemical identifier (e.g., formula or sequence 408) rather than the coded form.

In the illustrated embodiment, the CEDO having the smallest distance (greatest similarity) to the weighed vector is displayed in the node as the representative member of each cluster. In an alternative embodiment, additional or alternative chemical identifiers or other data elements of the CEDOs can be output by the visualization module for review by a user based on one or more user-selectable criteria, including interaction with individual nodes, data objects, or menus provided by an interface in communication with the visualization module 360.

In an alternative visualization, the marker clusters can be depicted as pie charts. In this embodiment, the relative presence of a desired element of each CEDO is shown. In FIG. 5C, the segments of the pie chart illustrate the number of CEDOs belonging to a specific source document.

In the provided visualization, it should be understood that the space between the clusters of markers 405 is non-linear. This is an artifact of the plot, which has the appearance of a 2-dimensional array, being an n-dimensional manifold space. The distances between clusters of markers is non-linear from node to node and so that true topology is obscured in the plot, but can be visually represented, in accordance with an aspect of the invention, using specially configured grid lines. Thus, in one embodiment of the system, relative distances between clusters can be represented by the presence, color and/or thickness of grid lines 410. For example, if grid lines are provided, the darker the grid lines, the greater the distance between each of the clusters 405. As another example, color coding can be used to represent closeness (red) and separateness (blue) with a spectrum in-between. The visualization module can include code that executes in the processor to support any of these, or other alternative visualization techniques.

In a further embodiment, the visualization module 360 comprises code that configures the processor to display CEDO data as a function of time. For example, the visualization module can configure the processor to display a time series of plots, where each of the elements of the series relates to the CEDOs from a common assignee at a given period in time. In this arrangement, the visualization module is configured by code executing in the processor to produce time-series animations based upon, among other features, the publication, issue, grant, or license of the underlying source documents linked to the CEDOs.

With reference to the 5D, the n-dimensional space is visualized as a grid 400 containing nucleotide sequences. In an alternative arrangement, amino acid sequences are provided. For clarity, when larger sequences are the subject the analysis, only a portion of the sequence can be shown. In another arrangement only the sequence at a particular location, e.g. complementary determining regions, is shown.

The n-dimensional mapping of the biologic information can be used to determine new biologic identifiers not disclosed in the original search results as in step 270. In one example, a plotted BDO in a first node of the n-dimensional map is compared to a second plotted BDO to determine the similarity of the sequences and to predict a new sequence that shares features of both sequences. In a particular approach, the prediction step 270 uses a common biological feature sub-module ("BF") that configures the processor to align the sequences for optimal comparison purposes (e.g., gaps can be introduced in the sequence of a first amino acid or nucleic acid sequence for optimal alignment with a second amino acid or nucleic acid sequence).

Here, when a position in the first sequence is occupied by the same amino acid residue or nucleotide as the corresponding position in the second sequence, then the molecules are identical at that position. In one arrangement, the percent identity between the two sequences is a function of the number of identical positions shared by the sequences (i.e., % identity=number of identical overlapping positions/total number of positions×100%). The determination of percent identity between two sequences can also be accomplished using a mathematical algorithm. A non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877, which are implemented in various BLAST and derivative programs, each of which is incorporated by reference as if fully set forth in its entirety herein.

Upon identification of non-similar portions of the sequence, the prediction module 370 can implement a modification process that replaces, deletes, adds or otherwise modifies either the first node sequence or the second node sequence in order to generate a new sequence not found in the n-dimensional space.

For example, the submodule can implement a substitution of amino acids within an amino acid sequence such that amino acid members of the same groups: (1) acidic (negatively charged) amino acids, such as aspartic acid and glutamic acid; (2) basic (positively charged) amino acids, such as arginine, histidine, and lysine; (3) neutral polar amino acids, such as glycine, serine, threonine, cysteine, tyrosine, asparagine, and glutamine; (4) neutral nonpolar (hydrophobic) amino acids, such as alanine, leucine, isoleucine, valine, proline, phenylalanine, tryptophan, and methionine; (5) amino acids having aliphatic side chains, such as glycine, alanine, valine, leucine, and isoleucine; (6) amino acids having aliphatic-hydroxyl side chains, such as serine and threonine; (7) amino acids having amide-containing side chains, such as asparagine and glutamine; (8) amino acids having aromatic side chains, such as phenylalanine, tyrosine, and tryptophan; (9) amino acids having basic side chains, such as lysine, arginine, and histidine; (10) amino acids having sulfur-containing side chains, such as cysteine and methionine; and (11) amino acids having similar geometry and hydrogen bonding patterns, such as aspartic acid, asparagine, glutamic acid and glutamine, may be substituted for one another based on the sequence and the properties of each amino acid. Similar substitutions can be made for nucleotides, or peptides to achieve new biologic identifiers not described in the search results.

The resulting newly generated sequence is placed into map and the location noted. In the event that newly generated sequence is placed in the desired location, such as an empty node 406, the process is complete. However, when the newly generated sequence results in a non-desired placement, the process can precede iteratively until a sequence resulting in the desired placement is generated.

Once new sequence is generated, it can be synthesized. In one instance, the synthesis is carried out using hybridoma processes and procedures or other similar techniques.

In a still further embodiment, the visualization module 360 further includes a statistical analysis sub-module. This sub-module configures the processor, in one implementation, to cooperate with the time-based data to produce predictions and evaluations of the data. For example, the statistical analysis sub-module comprises code executing in the processor to configure the processor to evaluate collections of time-series data across the collection of CEDOs and generate predictive models of how and how many source documents are generated over time that relate to particular biological targets and other associated data, or to any other subject matter of interest that is being visualized.

In one implementation, the statistical analysis sub-module configures the processor to implement one or more linear classifier algorithms (e.g. Support Vector Machine Algorithm, Naïve Bayes Classifier, unsupervised learning algorithms and/or logistic regression) on data related to the CEDOs. In one implementation, the unsupervised learning algorithm (e.g., the self-organizing map algorithm previously described) is determines, using code that configures the processor, how a portfolio of CEDOs owned by an entity is developed over time, such as by identifying latent traits or parameters that are useful in predicting future development. For example, the processor implements an unsupervised learning algorithm to evaluate the changes in chemical identifiers described in source documents owned by an entity over time and extracts predictive information related to the changes. In another arrangement the processor is configured by code to evaluate the change in the number of nodes occupied by chemical identifiers described in source documents owned by an entity over time and to identify variables or parameters that are statistically linked to the change in the number of nodes. In these manners, predictive models can be generated and utilized by the statistical analysis sub-module.

Optional Visualization Module Features

The map produced by the visualization module is adjustable based on additional user defined variables. For example, the display of CEDOs on the map can be filtered according to information relating to the source document or bibliographic information. In one arrangement, the map is configured to only display CEDOs from patent owners that have a certain financial position, such as profitability, or negative balance sheets. These additional data features are accessible through the source documents, or through third party databases that provide information corresponding to the inventors, assignees, owners, or licensees of specific or classes of CEDOs. In this regard, the system can link databases other than, say, patent and literature databases, in order to produce a map informed by another type of database, say, a financial database such as those available from Thomson Reuters or Bloomberg, Inc.

In a further visualization, the map is configured to display the results representing the analysis of multiple subject areas. For example the CEDOs originating from searches relating to different subject matters are visualized in a single 2 dimensional map. In this arrangement, the node array will contain CEDOs relating to a number of subject matter targets (e.g. sodium channel inhibitors, potassium channel inhibitors, etc.).

Discussion of a Prediction Module

In a more particular aspect that can be implemented in certain embodiments of the invention, a predictive analysis is conducted on the organized data. In the illustrated block diagram of FIG. 3, a prediction module 370 is implemented after the visualization module 360. Once the data has been organized by the modules, a predictive analysis can be performed before, or in lieu of, the visualization steps.

Referring again to FIG. 3, the prediction module 370 can comprise code which executes to configure the processor to predict, as indicated at step 270, at least one new chemical entity. In embodiments that include the visualization module, the new chemical entities that are predicted can be inserted into the n-dimensional space based on the results of the plotting module 340, utilizing the iterative insertion as described in step 250, into a desired location of the plot. For example, the user might select any empty node as the desired location, or might select a sparsely populated node, or might select an adjacent node as a location of interest. Alternatively, in an embodiment of the present invention that uses a non-node based dimensionality reduction technique, a coordinate location that is not currently occupied or that is of particular interest is selected in the continuous 2- or 3-dimensional space. Such selections can be made by interacting with the virtual node array as by manipulating a pointer or otherwise identifying a location within a graphical user interface that is presently displaying the virtual node array, or using a rule-based node selection algorithm. When locations are selected made using rule-based approaches, computational resources are allocated for the subject matter of interest (e.g., new chemical entity discovery) at locations in the landscape associated with rule-based discovery objectives, rule-based constraints on the new subject matter possibilities, or both, which improves the efficiency of the computer and of the downstream clinical investigation of any newly identified subject matter (e.g., new chemical entities) by focusing the machine's operation.

Operation of the prediction module results in the new chemical entity having a location within the plot, and if that location is in the selected node (i.e., an empty or sparsely populated node), or is in a coordinate location of interest, then the process can stop with a new chemical entity having been identified, as described further below. Alternatively or in addition, utilizing the iterative insertion as described in step 250, the prediction module can operate to test the location of a plurality of specific chemical structures having the identified common CS features for a fit into a desired location in the virtual array. For the avoidance of doubt, operation of the prediction module can be in regard to a static virtual array, meaning, as a predicted entity is assigned a location within the virtual array, the landscape need not be retrained and the entities assigned to nodes or coordinate locations within the landscape can remain in position unperturbed by the testing of specific chemical structures for their respective fit within the virtual array. The prediction module 370 can further include code that causes the processor to generate and predict chemical identifiers to add to an established population of representational data (e.g. CEDOs, nucleotide sequences, n-grams) that have been plotted to a 2-dimensional node map.

Figure 6:
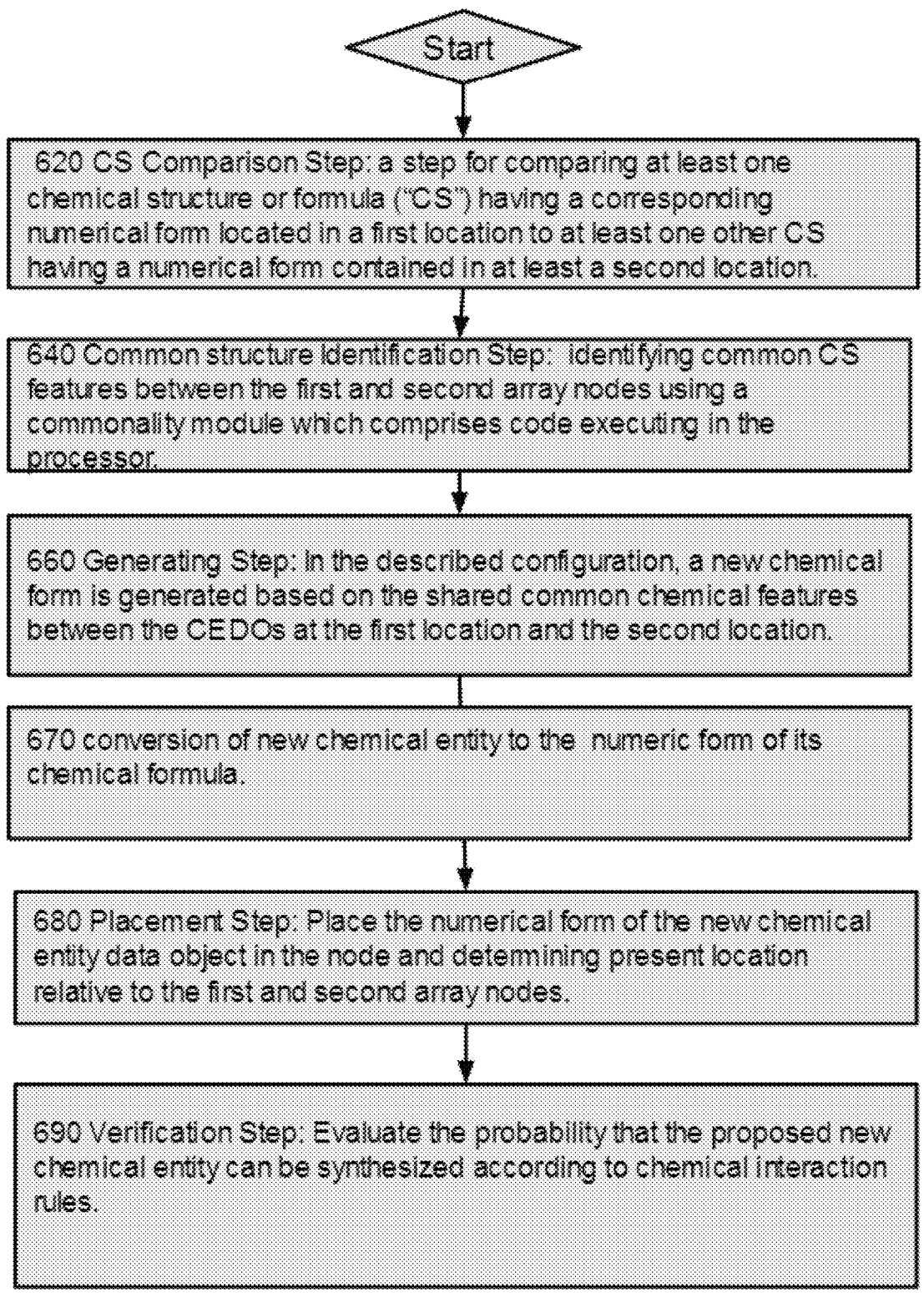
FIG. 6 is a diagram of the operation of the new chemical entity generating module according to certain embodiments of the system described.

More generally, the prediction module 370 configures the processor to implement a series of steps. In one non-limiting example, as shown in FIG. 6, the steps carried out by the processor configured by the prediction module generate a new chemical entity formula based on the results of the plotting module. The prediction module implements a comparison step 620 to compare the chemical identifier, such as a chemical structure or formula ("CS") or other chemical identifier of a CEDO located in one node to another CEDO located in a different node. For example, the CEDO locations can be array nodes generated by a self-mapping algorithm. In a further embodiment the first and second nodes share a border with each other or with a common third node. In an alternative embodiment, the first and second location nodes are, instead, first and second coordinates points in virtual n-dimensional manifold, when the virtual n-dimensional manifold is generated using a non-node based dimensionality reduction technique of the virtual array to another CEDO located in a different node of the virtual array.

In an arrangement utilizing other representational data, the commonalities present between the coded forms of representational data found in adjacent nodes are used as a basis to generate new representational data not found in the manifold. For instance, the commonalities between nucleotide sequences are used to generate a new nucleotide sequence not described in the source documents, that when converted into the coded form occupies a desired location in the node array.

In one specific embodiment, the user selects a specific node as a starting point for the prediction module 370. In an alternative configuration, the prediction module 370 includes a target sub-module that configures the processor to automatically select a target node for analysis. For example, the target sub-module is configured to select as a target any empty node in the virtual array. Alternatively, the target sub-module configures the processor by code executing in the processor to select as a target any empty node that shares borders with the nodes filed with coded forms of representational data, here CEDOs, having the same bibliographic information. In a further arrangement, the target node is selected based on external content obtained from the external content sub-module.

For example, the CEDO locations are virtual array nodes generated by a self-mapping algorithm. In a further embodiment, the first and second nodes share a border with each other or a common third node in the virtual array. In an alternative embodiment, the first and second location nodes instead comprise first and second coordinates points in a virtual n-dimensional space, when the n-dimensional space is generated using a non-node based dimensionality reduction technique to define that landscape.

Discussion of Common Feature Identification

In a further embodiment, the processor is configured to implement a common CS feature identification, as indicated at step 640. According to step 640, the chemical features for the CEDOs of the first and second location in the virtual array are identified. In one embodiment, the processor implements an algorithm configured to extract the number and form of chemical sub-units of which the compound is composed. This can include chemical features corresponding to Murcko derived scaffolds, graphs and molecular frameworks.

In an alternative embodiment, an image processing system ("IPS," not shown) can be used to extract common structural elements between the first and second numerical forms. An IPS can capture a segment of the map (e.g., a node) and characterize the CS based on the image using rules that match the features within the target viewing area (such as ring structures, single and double bonds, and so on).

Figure 7A:
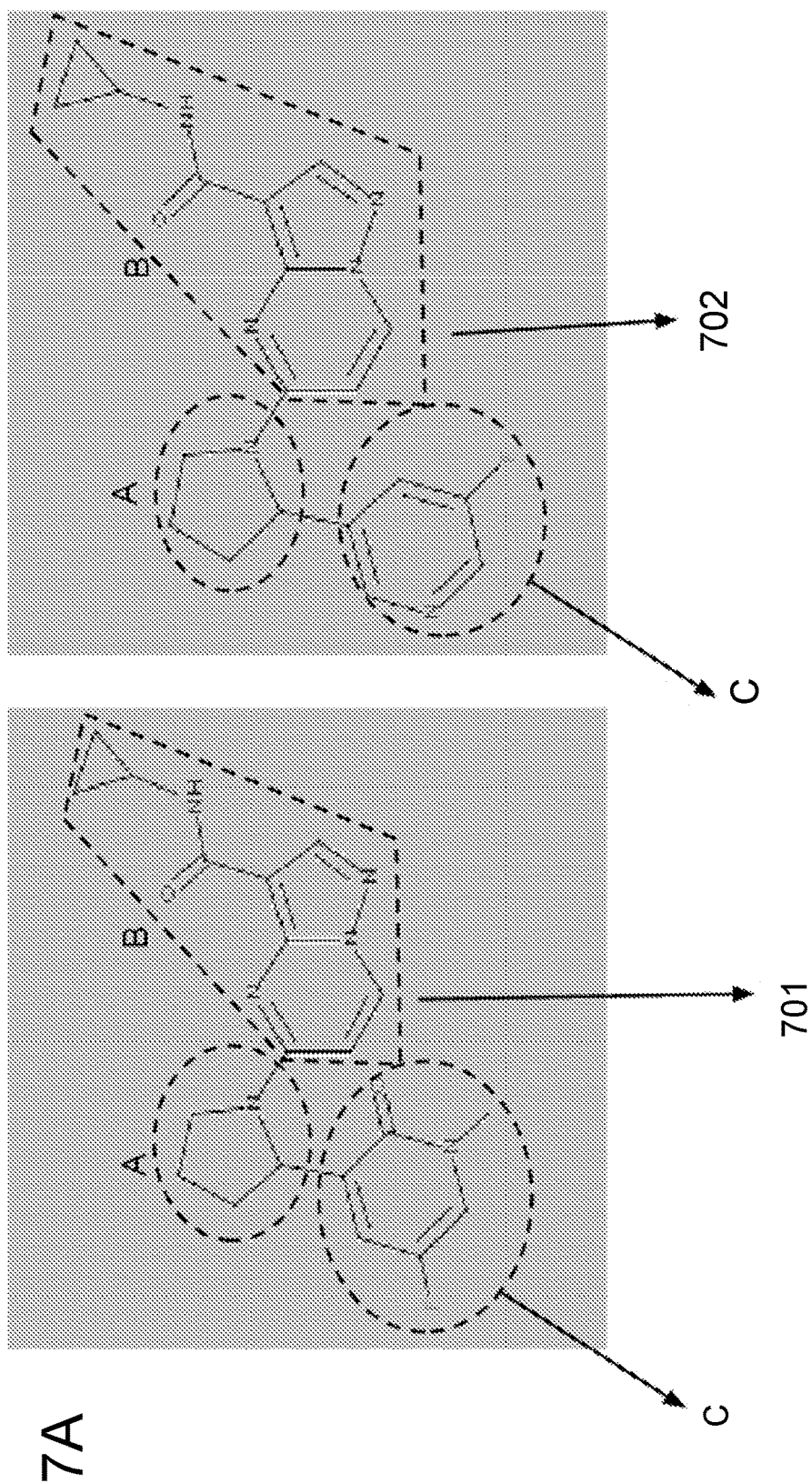
FIG. 7A is a detailed view illustrating common structural elements of nearby or adjacent nodes of a visualization map.

FIG. 7A illustrates two sample chemical forms sharing a common border with a third, empty node, as determined by a self-organizing mapping algorithm. The chemical forms illustrated, for example, include the types of features that an IPS can be programmed to recognize. As shown in FIG. 7A, the common structural forms of first chemical structure 701 and second chemical structure 702 are analyzed, such as by an image processing algorithm comprising code executing in the processor 102 to configure the processor to extract the structural features that are in common with both. In this embodiment, the processor identifies common structures (A, B) and non-common structures C, according to a look-up table or a database of known or expected chemical structures, and optionally using rules that govern how the processor is to process the structural forms.

Returning to FIG. 6, the predictive module is further configured to implement within a processor a new chemical form generation, as indicated at step 660. In the described embodiment, a new chemical form is generated based on the shared common chemical features between the CEDOs at the first location and the second location of the virtual array. In particular, the new chemical form is generated by replacing sub-units of the common chemical's structural features. Alternatively, the new chemical form is generated by selecting, augmenting or modifying the non-similar chemical sub-units and combining those units with the commonly identified structural features. In a one particular embodiment, a chemical formula is generated corresponding to the new chemical form.

In arrangements using other forms of representational data, such as nucleotide or amino acid sequences, common features are identified by sequence similarity tools such as BLAST or other software platforms that allow the system to find regions of similarity between biological sequences. Likewise, in non-biological sequences, such as n-gram analysis, common features found in the corpus are the starting point for generating new representational data for inclusion within the nodes of the visualization. For example, to determine the similarity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877 incorporated by reference as if fully set forth in its entirety herein. Such an algorithm is incorporated into the NBLAST and XBLAST programs of Altschul et al., 1990, J. Mol. Biol. 215:403 incorporated by reference as if fully set forth in its entirety herein.

As used herein, step 660 can implement a substitution of amino acids within a amino acid sequence such that amino acid members of the same groups: (1) acidic (negatively charged) amino acids, such as aspartic acid and glutamic acid; (2) basic (positively charged) amino acids, such as arginine, histidine, and lysine; (3) neutral polar amino acids, such as glycine, serine, threonine, cysteine, tyrosine, asparagine, and glutamine; (4) neutral nonpolar (hydrophobic) amino acids, such as alanine, leucine, isoleucine, valine, proline, phenylalanine, tryptophan, and methionine; (5) amino acids having aliphatic side chains, such as glycine, alanine, valine, leucine, and isoleucine; (6) amino acids having aliphatic-hydroxyl side chains, such as serine and threonine; (7) amino acids having amide-containing side chains, such as asparagine and glutamine; (8) amino acids having aromatic side chains, such as phenylalanine, tyrosine, and tryptophan; (9) amino acids having basic side chains, such as lysine, arginine, and histidine; (10) amino acids having sulfur-containing side chains, such as cysteine and methionine; and (11) amino acids having similar geometry and hydrogen bonding patterns, such as aspartic acid, asparagine, glutamic acid and glutamine, may be substituted for one another based on the sequence and the properties of each amino acid.

Selecting and obtaining chemical formulas based on the known chemical structures of each CEDO is not limited to image analysis functions. There exist a number of different computational chemistry methodologies, including but not limited to: scaffold-hopping, and other bioisosteric replacement techniques such as fragment replacement, computer assisted organic synthesis methods, Ab initio methods, density functional methods, semi-empirical and empirical methods, molecular mechanics, molecular dynamics methods, any of which can be used to determine the form of the new chemical entity.

In a further arrangement, any new chemical forms generated according to the above steps are then subject to a pharmaceutical suitability analysis, such as by evaluating proposed chemical forms using Lipinski's Rule of Five, or another drug likeness rule to determine if the proposed chemical entity has properties that would make it likely to be orally active in humans.

As shown in FIG. 6, the processor executing the prediction module is further configured to convert the new chemical entity chemical formula to a coded form according to the conversion step, as indicated at step 670. In a particular embodiment, the processor converts the chemical form using a specified key-digit solution suitable for use in the dimensionality reduction algorithm being used in that particular embodiment of the invention. The prediction module 370 further configures the processor to implement a placement step 680 to place the numeric form of the new chemical entity in a given location of the n-dimensional space of the virtual node array. Upon placement in the virtual node array, if the numerical form is located in the desired coordinates of the plot, then the processor associates the new chemical form with a unique visual marker and updates the visualization. Again, the "desired coordinates" could be those coordinates which are between the first and second virtual nodes, within the first or second virtual node, or within a third node in the virtual array which shares a border with the first and second virtual nodes.

Alternatively, if the newly formed chemical entity does not result in placement in the desired coordinate space, then the processor can be configured by further code, such as in an iterative sub-module, to generate new chemical entities. This iterative process is controlled by the processor and is configurable to continue generating new chemical entities until one of the entities, when converted into a coded format and inserted into the node, results in the desired placement has been generated, or, alternatively, until a pre-set time limit, or number of attempts has been met or exceeded. In a further embodiment, each newly generated coded form that fails to have the desired placement in the virtual node array is stored in a memory storage location for later retrieval and use by the system.

In a further embodiment, each newly generated coded form that fails to have the desired placement, or placement within a neighborhood of the desired placement, is stored in a memory storage location for later retrieval and use by the system. One subsequent use for a failed coded form in regard to a previously trained and created landscape can include noting a distance from the desired node or coordinate location and using that distance metric to optimize a subsequent analysis of proposed new chemical structures having common features. For example, if the distance metric is greater than a threshold value or threshold percentage of a reference distance value, then the prediction module 370 can use the stored data to more optimally test proposed structures that are to be fit to the landscape.

In a further aspect, the prediction module can configure the processor to implement a verification step 690. In an embodiment that includes this step, the processor executes instructions in order to evaluate the probability that each chemical identifier of each newly generated chemical entity is able to be synthesized. In a particular embodiment, the verification step 690 compares the chemical formula of the new chemical entity to a database of known chemical structure, structural interactions and/or chemical reactions and formulae. According to this embodiment, each new chemical identifier is evaluated for the probability of successful synthesis, e.g., whether it is above a pre-set threshold. The synthesis probability is provided by the processor to the user as part of the visualization update. The probability evaluation can utilize stochastic algorithms to identify subsets of NCEs that are more likely to be synthesizable. In one embodiment, only synthesis probabilities above the pre-set threshold are provided as part of the visualization update.

Figure 7B:
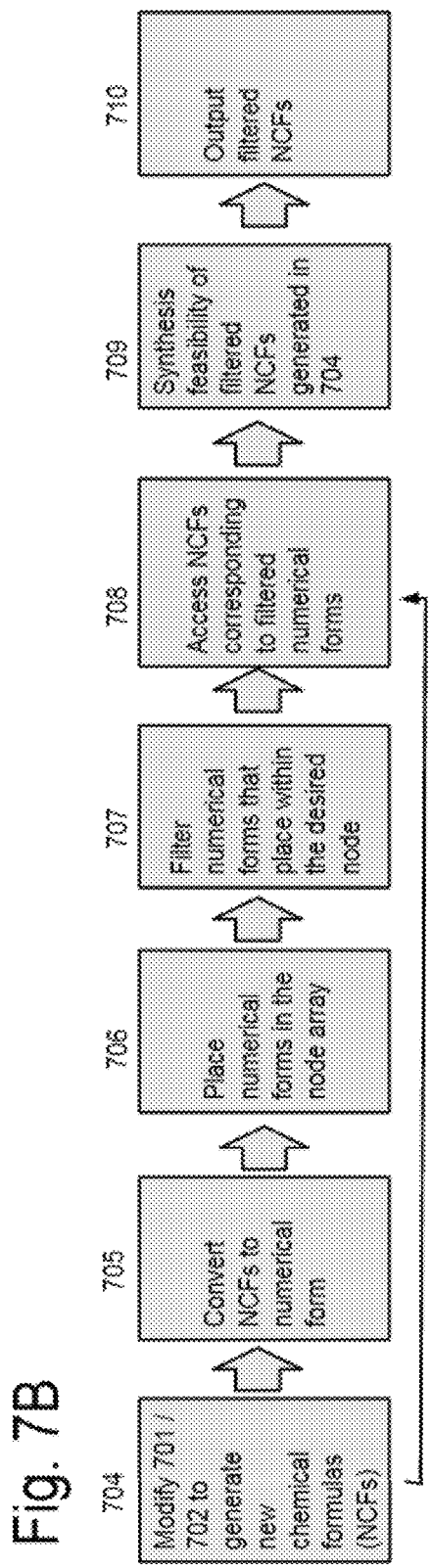
FIG. 7B is a flow diagram in accordance with certain embodiments of the invention.

The verification as to whether a predicted chemical entity can be synthesized can be informed by chemical synthesis machines, such as the Revblocks™ platform being developed or offered by Revolution Medicines of Redwood City, Ca. Platforms such as this are said to synthesize original compounds. Turning to FIG. 7B, a detailed example of the predictive portion of the system described is in connection with a flow diagram. Step 704 follows the generation of new chemical formulae for insertion into the node map based on chemical formulae of neighboring nodes (chemical structures 701 and 702). The processor, configured by the prediction module code, generates a new chemical identifier, such as a new chemical formula (NCF), by modifying the chemical formula of sub-unit C (FIG. 7A) according to known chemical rules and libraries.

Once NCFs are generated, they are converted by the processor into numerical forms as in step 705. The converted forms are then placed in the node array stored in the memory of the processor, as in step 706. Furthermore, the processor is configured by code to filter the NCFs, selecting only those that result in placement in the node array at a desired coordinate location in the virtual array, as shown in step 707.

Discussion of Synthesis of Newly Identified Subject Matter

Step 708 details the actions taken by the processor to access, from a database or other memory storage location, the original NCFs corresponding to the filtered coded forms. In step 709, the processor is configured by code to evaluate the NCFs in light of stored or accessible chemical synthesis rules in order to determine likelihood of synthesis. The processor is further configured by code executing therein to output NCFs with a synthesis probability above a threshold to a visualization module for display, as indicated at step 710. A collection of new chemical entities with associated synthesis probabilities can be presented to a user as a visualization within the virtual array of the stored chemical identifiers in the storage location. Alternatively, a user supplied metric, such as synthesis time, cost, or difficulty is implemented and used to filter the results displayed or provided to the user.

In yet a further embodiment, the prediction module configures the processor to predict a location of potential interest within the virtual array and generate a new chemical formula corresponding to that location. In one example, the prediction module is configured to generate a time series plot indicating the publication of source documents over time. In a further example, the prediction module is configured to extrapolate, based, e.g., on the rate of publications of source documents, a development path for a common inventor or assignee. The system described may be configured to generate a new chemical entity which, when placed in the virtual array, occupies a location in line with the development path or which is clear of that path.

In a further embodiment, the prediction module is configured to extrapolate a location or locations in the virtual node array at which the development path of a plurality of assignees or inventors will intersect, and generate a chemical formula which, when placed in the virtual array, occupies or is clear of that intersection location.

As a further embodiment of the system and method of the present invention, the processor is further configured by code to generate a synthesis strategy along with the new chemical identifier, such as may occupy or be clear of a development path of one or more assignees, inventors, and so on, as discussed above. For instance, the new chemical formula generation step 660 includes sub-steps designed to generate a synthesis strategy or plan based on organic compound synthesis analysis of the desired chemical compound described by the new chemical identifier.

The techniques for utilizing and designing computer-assisted synthesis strategies include, by way of non-limiting example, computer based retrosynthetic analysis. For example, "Route designer: a retrosynthetic analysis tool utilizing automated retrosynthetic rule generation" James Law, et al., J. Chem. Inf. Model., 2009, 49 (3), 593-602, the content of which is hereby incorporated by reference in its entirety, describes the utilization of software tools and processes to generate a proposed chemical synthesis strategy based on breaking down of a chemical identifier into idealized compound fragments. These idealized compound fragments are substituted with synthetic equivalents having known synthesis strategies and have similar characteristics to the characteristics of the idealized fragments, e.g., the same elemental composition, binding affinity, etc., according to a database of chemical data. In this way, the software tool can execute to cause a processor to provide a synthesis strategy for the new chemical identifiers using synthesis pathways already known in the art.

In the event that the idealized compound fragments do not have known synthetic equivalents, these idealized components are broken down into smaller fragments until the synthesis of each of the fragments, or their substituted synthetic equivalents are described in a database of synthesis strategies or pathways. Thus, the synthetic pathway to achieving the new chemical entity is derived using the new chemical entity identifier in lieu of a process of trial and error using common starting reactants.

In one potential arrangement, the fragment data used to determine the synthesis are the same fragment data used to generate the new chemical entity. For example, each of the modified sub-units (See C in FIG. 7A) used to generate the new chemical identifier are utilized as idealized or synthetic equivalent fragments in order to determine a synthesis pathway of the resulting new chemical entity. Owing to the fact that the sub-units utilized to generate the new chemical entity are known, they are derived in part from the chemical database associated with a given embodiment of the system. As a consequence, embodiments of the present invention allow for the generation of both the new chemical entity as well as a synthesis solution to synthesize the chemical compound. In other embodiments, different strategies for synthesizing or designing a usable synthesis strategy, such as, but not limited to, functional group analysis, stereo-chemical and chirality analysis, structure-goal seeking strategies, topological analysis strategies and transform-based strategies can be employed to synthesize a chemical compound described by the chemical identifier.

In one arrangement, once a chemical formula and the synthesis strategy are generated, this information is then used to synthesize the chemical compound described by the chemical formula or identifier according to the synthesis strategy.

For example, in one particular embodiment of the invention, the new chemical entity identification method includes a further synthesis step, carried out to enable synthesizing a compound described by the newly generated chemical identifier. In a further embodiment, when the newly generated chemical identifier is intended to have a therapeutic effect on a biological organism, a further step includes preparing a pharmaceutical composition comprising an effective amount of the chemical compound corresponding to the new chemical formula generated according to the chemical entity generation module, or an acceptable salt thereof, and a pharmaceutically acceptable excipient. A further step can include coating the so-prepared composition, such as with an enteric coating. The method can include a variety of additional steps to prepare the composition in a form suitable for administration to a person.

In a further arrangement, the chemical compounds are synthesized using a device or machine configured to implement continuous-flow multi-step organic compound synthesis utilizing a feed stock of standard reactants commonly used in the type of synthesis reactions necessary to achieve the desired end chemical compound. For example, the processor of the present invention can be further configured to provide instructions to a computer controlled continuous flow reactor, such the chemical compound described by the new chemical entity identifier is synthesized according to a retrosynthetic plan determined by a synthesis plan module configured as code executing within the processor.

The above processing functions can operate as a series of programmed steps performed by a properly configured computer system using one or more modules of computer-executable code. For instance, a set of software modules can be configured to cooperate with one another to provide prediction information regarding new chemical entities to a display device as described herein. In this regard, there can be a database access modules, search modules, filtering modules, extraction modules, conversion modules, plotting modules, prediction modules, and visualization modules.

Each of these modules can comprise hardware, code executing in a computer, or both, that configure a machine such as the computing system 100 to implement the functionality described herein. The functionality of these modules can be combined or further separated, as understood by persons of ordinary skill in the art, in analogous embodiments of embodiments of the invention.

The processor 102 of the described invention is configurable for connection to remote storage devices and computing devices. For example the processor of the described computer system may, in one embodiment, be configured for communication with a mobile computing device, or connecting via the internet to a remote server.

As illustrated in FIG. 8, the computing system 1300 and includes a processor 1302, a memory 1304, a storage device 1306, a high-speed interface 1308 connecting to the memory 1304 and multiple high-speed expansion ports 1310, and a low-speed interface 1312 connecting to a low-speed expansion port 1314 and the storage device 1306. Each of the processor 1302, the memory 1304, the storage device 1306, the high-speed interface 1308, the high-speed expansion ports 1310, and the low-speed interface 1312, are interconnected using various buses, and can be mounted on a common motherboard as shown in FIG. 8, or in other manners as appropriate. The processor 1302 can process instructions for execution within the computing device 1300, including instructions stored in the memory 1304 or on the storage device 1306 to display graphical information for a GUI on an external input/output device, such as a display 1316 coupled to the high-speed interface 1308. In other embodiments, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

A mobile computing device 1350 may include a processor 102, a memory 1364, and an input/output device such as a display 1354, a communication interface 1366, and a transceiver 1368, among other components. The mobile computing device 1350 can also be provided with a storage device, such as a micro-drive or other device, to provide additional storage. Each of the processor 1352, the memory 1364, the display 1354, the communication interface 1366, and the transceiver 1368, are interconnected using various buses, and several of the components can be mounted on a common motherboard or in other manners as appropriate.

The processor 1352 can communicate with a user through a control interface 1358 and a display interface 1356 coupled to the display 1354. The display 1354 can be, for example, a TFT (Thin-Film-Transistor Liquid Crystal Display) display or an OLED (Organic Light Emitting Diode) display, or other appropriate display technology. The display interface 1356 can comprise appropriate circuitry for driving the display 1354 to present graphical and other information to a user. The control interface 1358 can receive commands from a user and convert them for submission to the processor 1352. In addition, an external interface 1362 can provide communication with the processor 1352, so as to enable near area communication of the mobile computing device 1350 with other devices. The external interface 1362 can provide, for example, for wired communication in some embodiments, or for wireless communication in other embodiments, and multiple interfaces can also be used.

The memory 1364 stores information within the mobile computing device 1350. The memory 1364 can be implemented as one or more of a computer-readable medium or media, a volatile memory unit or units, or a non-volatile memory unit or units. An expansion memory 1374 can also be provided and connected to the mobile computing device 1350 through an expansion interface 1372, which can include, for example, a SIMM (Single In Line Memory Module) card interface. The expansion memory 1374 can provide extra storage space for the mobile computing device 1350, or can also store applications or other information for the mobile computing device 1350. Specifically, the expansion memory 1374 can include instructions to carry out or supplement the processes described above, and can include secure information also. Thus, for example, the expansion memory 1374 can be provided as a security module for the mobile computing device 1350, and can be programmed with instructions that permit secure use of the mobile computing device 1350. In addition, secure applications can be provided via the SIMM cards, along with additional information, such as placing identifying information on the SIMM card in a non-hackable manner.

It should be understood that various combinations, alternatives and modifications of the present invention could be devised by those skilled in the art in view of this disclosure. The present invention is intended to embrace all such alternatives, modifications and variances that fall within the scope of the appended claims. While the invention has been particularly shown and described with reference to a preferred embodiment thereof, it will be understood by those skilled in the art that various changes in form and details may be made therein without departing from the spirit and scope of the invention.

The mobile computing device 1350 can communicate wirelessly through the communication interface 1366, which can include digital signal processing circuitry where necessary. The communication interface 1366 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1368 using a radio-frequency. In addition, short-range communication can occur, such as using a Bluetooth, WiFi, or other such transceiver (not shown). In addition, a GPS (Global Positioning System) receiver module 1370 can provide additional navigation- and location-related wireless data to the mobile computing device 1350, which can be used as appropriate by applications running on the mobile computing device 1350.

The mobile computing device 1350 can also communicate audibly using an audio codec 1360, which can receive spoken information from a user and convert it to usable digital information. The audio codec 1360 can likewise generate audible sound for a user, such as through a speaker, e.g., in a handset of the mobile computing device 1350. Such sound can include sound from voice telephone calls, recorded sound (e.g., voice messages, music files, etc.) and sound generated by applications operating on the mobile computing device 1350.

The mobile computing device 1350 can be implemented in a number of different forms, as shown in FIG. 8. For example, it can be implemented as a cellular telephone 1380. It can also be implemented as part of a smart-phone 1382, personal digital assistant, or other similar mobile device.

Various embodiments of the systems and techniques described here can be realized in digital electronic circuitry, integrated circuitry, specially designed ASICs (application specific integrated circuits), computer hardware, firmware, software, and/or combinations thereof. These various embodiments can include embodiment in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable storage medium and computer-readable storage medium refer to any non-transitory computer program product, apparatus and/or device (e.g., magnetic discs, optical disks, memory, Programmable Logic Devices (PLDs)) used to provide machine instructions and/or data to a programmable processor, including a machine-readable storage medium that receives machine instructions as a machine-readable signal. The term machine-readable signal refers to any signal used to provide machine instructions and/or data to a programmable processor. A non-transitory machine-readable storage medium does not include a transitory machine-readable signal.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server 1324), or that includes a middleware component (e.g., an application server 1320), or that includes a front end component (e.g., a client computer 1322 having a graphical user interface or a Web browser through which a user can interact with an embodiment of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific embodiment details, these should not be construed as limitations on the scope of any embodiment or of what can be claimed, but rather as descriptions of features that can be specific to particular embodiments of particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain embodiments, multitasking and parallel processing can be advantageous.

While the invention has been particularly shown and described with reference to a preferred embodiment thereof, it will be understood by those skilled in the art that various changes in form and details may be made therein without departing from the spirit and scope of the invention.

What is claimed is:

1. A computer-implemented method for generating an artificial environment within a memory of a computer, in which nucleotide identifiers that relate to a particular subject matter and which are described in at least one document are extracted and analyzed, the method comprising:
   submitting, in electronic form, a search to at least one document database for documents describing the subject matter using a defined search strategy;
   extrapolating, to a first array within the memory of the computer, at least one nucleotide described in at least one document returned from the search, the extrapolating step using an extraction module comprising code executing in a processor;
   transforming each nucleotide identifier in the first array into a respective coded vector form having a range of values using a conversion module comprising code executing in the processor;
   populating the respective coded vector forms into a second array within the memory of the computer;
   generating a virtual n-dimensional array of nodes configured to encompass the range of values in the second array using a node array generator module comprising code executing in the processor, each node of the virtual n-dimensional array having an associated weight vector value based on the range of values in the second array;
   placing each coded form in the second array into a node of the virtual n-dimensional array according to an unsupervised learning algorithm using a placement module comprising code executing in the processor to effect a placement;
      generating at least one new coded form and inserting it into the n-dimensional array within the target node using a coded form generator module which comprises code executing in the processor;
   determining a nucleotide identifier corresponding to the new coded form; and
   outputting the nucleotide identifier corresponding to the determined new coded form.

2. The method of claim 1, wherein generating at least one new coded form further comprising the steps of:
   selecting a target node among the nodes within the virtual n-dimensional array;
   comparing, using a biologic feature ("BF") module which comprises code executing in the processor, at least one BF corresponding to the coded form contained within a first node adjacent to the target node to at least one BF corresponding to the coded form contained in at least a second node adjacent to the target node, the first and second nodes sharing a border with the target node in the virtual n-dimensional array;
   identifying common and non-common BFs between the target and second nodes using a commonality module which comprises code executing in the processor;
   generating at least one new coded form based on combinations of the identified, common and non-common BFs which, when inserted into the virtual n-dimensional array, results in a placement within the target node, using a coded form generator module which comprises code executing in the processor.

3. The method of claim 1, wherein generating at least one new coded form further comprising the steps of:
   selecting a first node among the nodes within the virtual n-dimensional array;
   comparing, using a biological feature ("BF") module which comprises code executing in the processor, at least one BF corresponding to the coded form contained within the first node adjacent to at least one BF corresponding to the coded form contained in at least a second, adjacent node, the second node sharing a border with the first node in the virtual n-dimensional array;
   identifying common and non-common BFs between the first and second nodes using a commonality module which comprises code executing in the processor;
   generating at least one new coded form based on combinations of the common and non-common BFs identified, which when inserted into the virtual n-dimensional array, results in a placement within the first or second node using a coded form generator module which comprises code executing in the processor.

4. The method of claim 1, wherein generating at least one new coded form further comprising the steps of:
   selecting a first node among the nodes within the virtual n-dimensional array;
   comparing, using a biological feature ("BF") module which comprises code executing in the processor, at least one BF corresponding to the coded form contained within the first node adjacent to at least one BF corresponding to the coded form contained in at least a second node, the second node sharing a border with the first node in the virtual n-dimensional array;
   identifying common and non-common BFs between the first and second nodes using a commonality module which comprises code executing in the processor;
   generating at least one new coded form based on combinations of the identified, common and non-common BFs;
   regenerating the n-dimensional node array to encompass the range of values stored in the second array including the new coded form such that, when inserted into the regenerated virtual n-dimensional array, the new coded form is placed in a node situated between the first and second nodes, using a coded form generator module which comprises code executing in the processor; and
   outputting a biological identifier corresponding to the new coded form.

5. The method of claim 1, wherein generating at least one new coded form further comprising:
   generating a visual display indicating the addition of numerical forms to virtual n-dimensional array of nodes in the memory, wherein the addition of numerical forms concerns a common owner of one or more patent documents returned from the search, wherein the generating uses a time-series module comprising code executing in the processor;

generating, using a time series plotting module comprising code executing in the processor, a time series plot indicating the publication of the one or more patent documents over time;

extrapolating, with an extrapolating module comprising code executing in the processor and based on the rate of publication of the one or more patent documents and biologic identifiers extracted from the patent documents, a development path for an inventor or assignee; common to the patent documents returned from the search;

generating a new nucleotide identifier that when placed in virtual n-dimensional array of nodes occupies a node in the development path.

6. The method of claim 5, further comprising:
generating, with a synthesis design module configured as code executing on the processor to generate, based on the new nucleotide identifier, a synthesis strategy for synthesizing a biologic described by the biologic identifier.

7. The method of claim 6, further comprising:

synthesizing a biopharmaceutical corresponding to the new nucleotide biologic identifier generated according to the synthesis strategy.

8. The method of claim 1, wherein the nucleotide identifiers are, nucleotide sequences, or amino acid sequences.

9. The method of claim 1, wherein the particular subject matter is a form of cancer.

10. The method of claim 1, wherein the particular subject matter is a form of auto-immune disease.

* * * * *

UNITED STATES PATENT AND TRADEMARK OFFICE
CERTIFICATE OF CORRECTION

| | |
|---|---|
| PATENT NO. | : 11,609,917 B1 |
| APPLICATION NO. | : 16/111081 |
| DATED | : March 21, 2023 |
| INVENTOR(S) | : Paul Blake et al. |

It is certified that error appears in the above-identified patent and that said Letters Patent is hereby corrected as shown below:

On the Title Page

Item (73) "PURDUE PHARMA L.P., STAMFORD, CT (US)" should be -- ACCENCIO LLC, PHILADELPHIA, PA (US) --.

Signed and Sealed this
Ninth Day of May, 2023

Katherine Kelly Vidal
*Director of the United States Patent and Trademark Office*